US008773106B2

(12) United States Patent
Elder

(10) Patent No.: US 8,773,106 B2
(45) Date of Patent: Jul. 8, 2014

(54) CAPACITANCE DETECTION IN ELECTROCHEMICAL ASSAY WITH IMPROVED SAMPLING TIME OFFSET

(75) Inventor: David Elder, Inverness (GB)

(73) Assignee: Lifescan Scotland Limited, Inverness (GB)

(*) Notice: Subject to any disclaimer, the term of this patent is extended or adjusted under 35 U.S.C. 154(b) by 426 days.

(21) Appl. No.: 13/208,082

(22) Filed: Aug. 11, 2011

(65) Prior Publication Data

US 2011/0301861 A1    Dec. 8, 2011

Related U.S. Application Data

(63) Continuation-in-part of application No. 13/034,281, filed on Feb. 24, 2011, and a continuation-in-part of application No. PCT/GB2011/000267, filed on Feb. 25, 2011.

(60) Provisional application No. 61/308,167, filed on Feb. 25, 2010.

(51) Int. Cl.
*G01N 27/00* (2006.01)

(52) U.S. Cl.
USPC ............................. 324/71.1; 324/453; 702/19

(58) Field of Classification Search
USPC .............. 324/452, 453, 71.1, 76.11; 204/779; 702/19
IPC .......................................................... C12Q 1/68
See application file for complete search history.

(56) References Cited

U.S. PATENT DOCUMENTS

| | | |
|---|---|---|
| 6,179,979 B1 | 1/2001 | Hodges et al. |
| 6,193,873 B1 | 2/2001 | Ohara et al. |
| 6,284,125 B1 | 9/2001 | Hodges et al. |
| 6,413,410 B1 | 7/2002 | Hodges et al. |
| 6,475,372 B1 | 11/2002 | Ohara et al. |
| 6,716,577 B1 | 4/2004 | Yu et al. |
| 6,749,887 B1 | 6/2004 | Dick et al. |
| 6,856,125 B2 | 2/2005 | Kermani et al. |

(Continued)

FOREIGN PATENT DOCUMENTS

| | | |
|---|---|---|
| EP | 2138841 A2 | 12/2009 |
| WO | WO 03/069304 A2 | 8/2003 |
| WO | WO 2005/003748 A1 | 1/2005 |
| WO | WO 2008/051804 A2 | 5/2008 |

OTHER PUBLICATIONS

International Search Report for PCT/GB2011/000267, dated Sep. 29, 2011.

(Continued)

*Primary Examiner* — Vincent Q Nguyen

(57) ABSTRACT

A method and a system are provided to determine fill sufficiency of an electrochemical biosensor test cell by determining capacitance of the electrochemical test cell. In particular, the system samples an output signal from the chamber at a second sampling-time interval different than a first sampling-time interval such that a magnitude of each sampled output signal is measured at each succession of the second sampling-time interval instead of at the first time interval. The system determines a phase angle between an output signal and the oscillating input signal from the chamber based on the sampled output signal of the sampling step. The system calculates a capacitance of the chamber from the phase angle. A method is also provided to perform similar functionalities of the system.

23 Claims, 15 Drawing Sheets

(56) References Cited

U.S. PATENT DOCUMENTS

| | | |
|---|---|---|
| 6,863,801 B2 | 3/2005 | Hodges et al. |
| 6,872,298 B2 | 3/2005 | Kermani et al. |
| 6,890,421 B2 | 5/2005 | Ohara et al. |
| 7,045,046 B2 | 5/2006 | Chambers et al. |
| 7,195,704 B2 * | 3/2007 | Kermani et al. ........... 205/777.5 |
| 7,199,594 B2 | 4/2007 | Kermani |
| 7,291,256 B2 | 11/2007 | Teodorczyk et al. |
| 7,498,132 B2 | 3/2009 | Yu et al. |
| 2009/0301899 A1 | 12/2009 | Hodges et al. |

OTHER PUBLICATIONS

PCT Search Report, International Application No. PCT/GB2011/001211 dated Mar. 20, 2012, 4 pages.

International PCT Application No. PCT/GB2011/000267, Invitation to Pay Additional Fees and, Where Applicable, Protest Fees Dated Jun. 7, 2011, 5 pages, European Patent Office, Rijswijk, Netherlands.

* cited by examiner

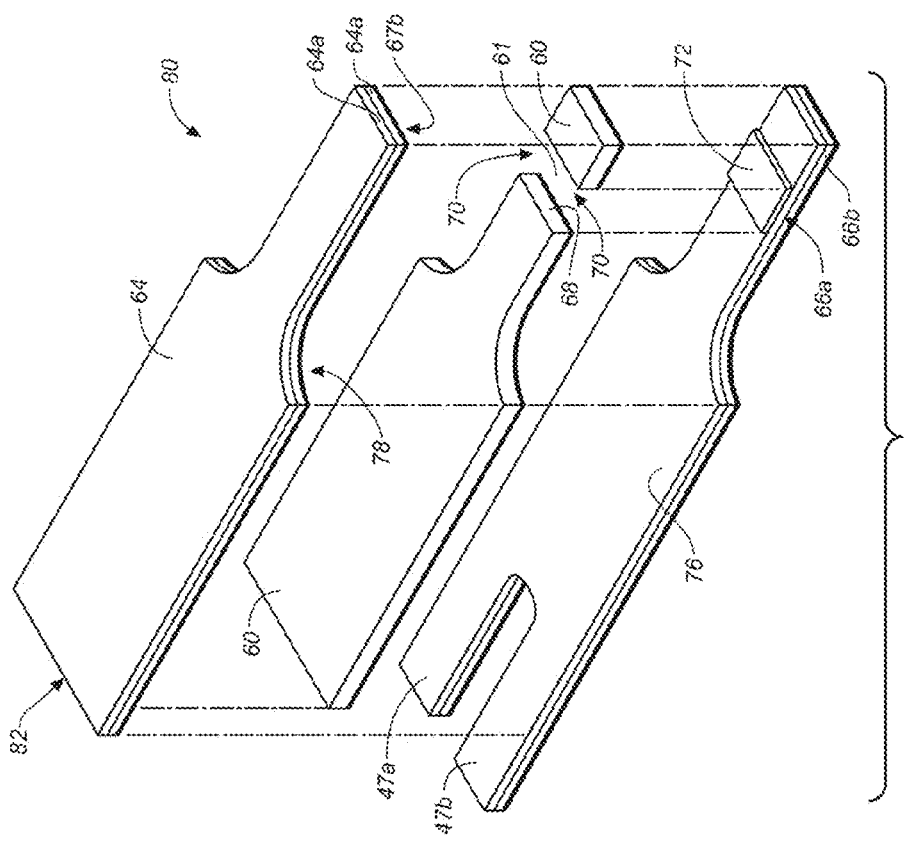
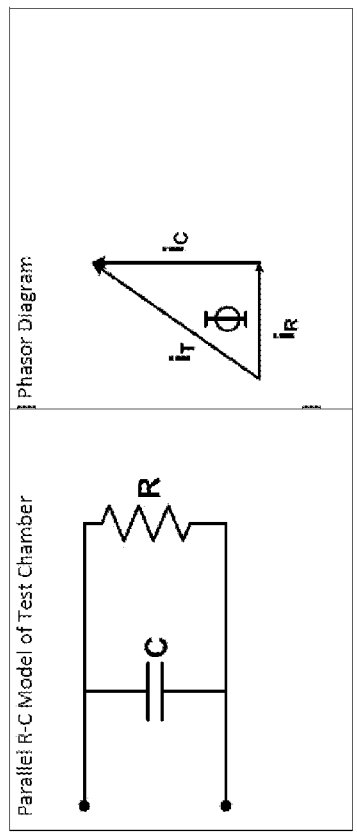
Fig. 3A
Fig. 3B

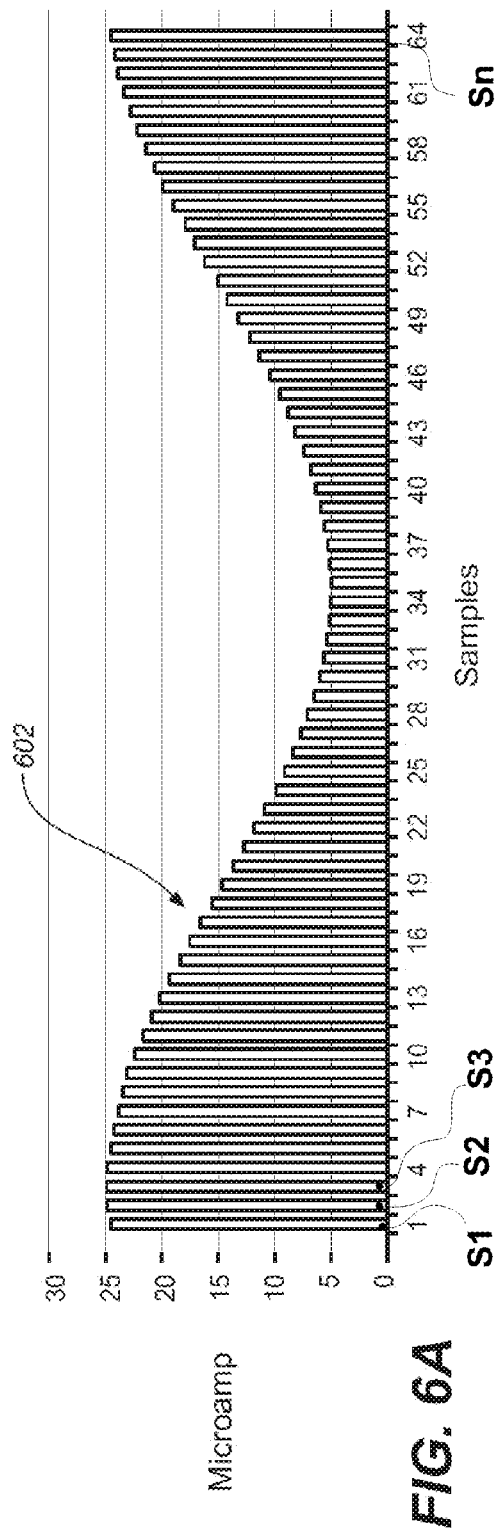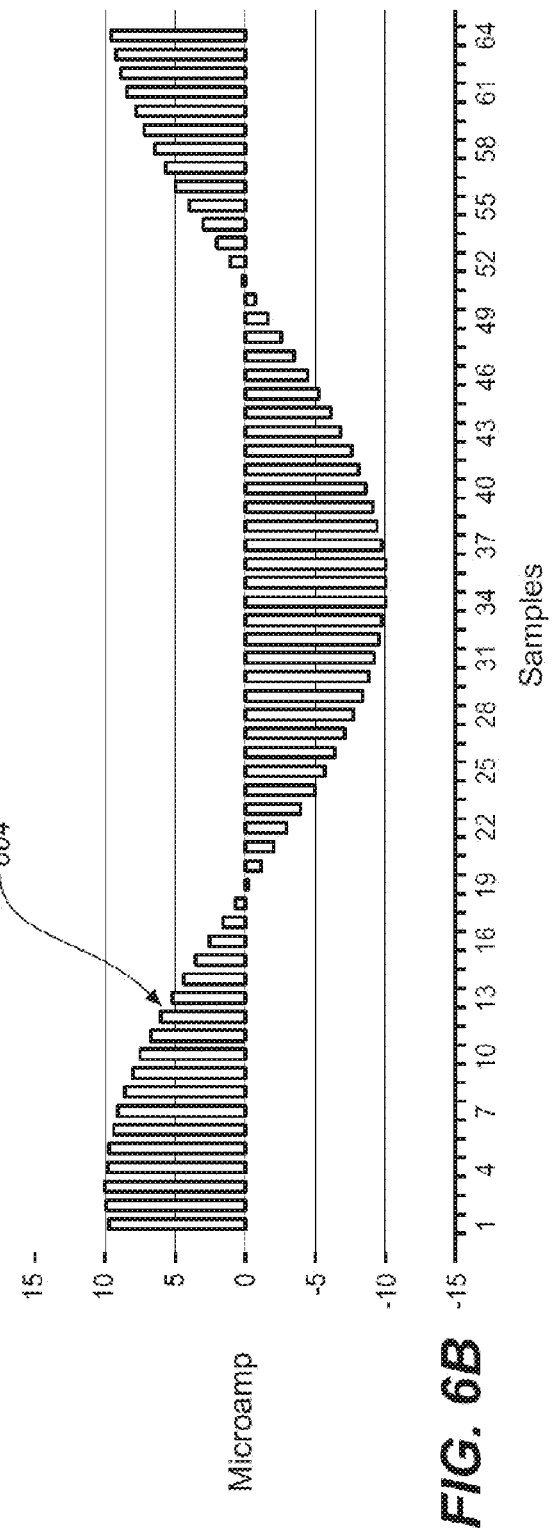
FIG. 6A
FIG. 6B

*FIG. 6C*
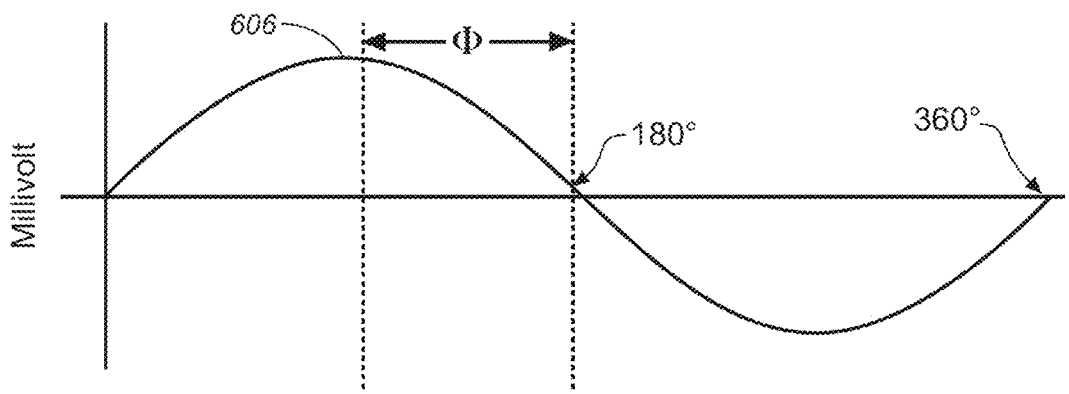
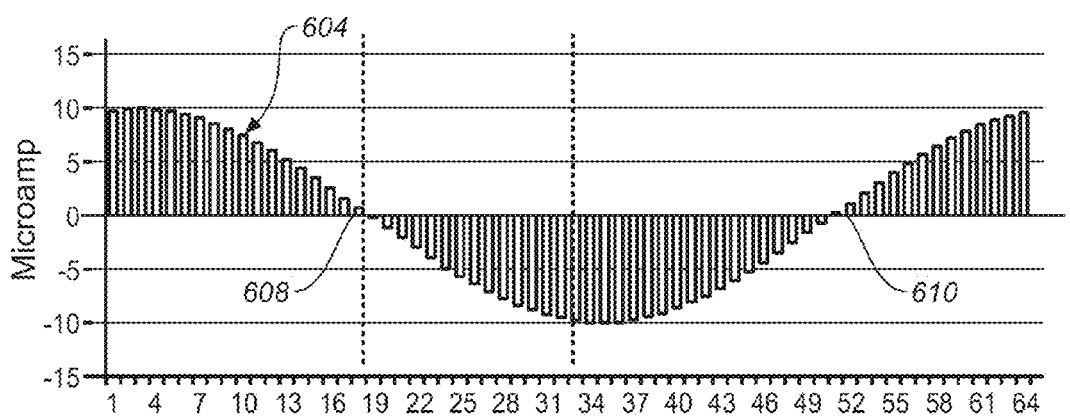
*FIG. 6D*
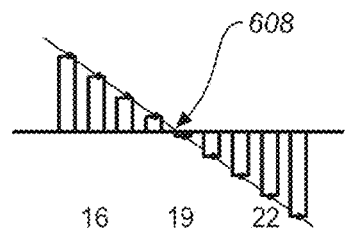
*FIG. 6E*

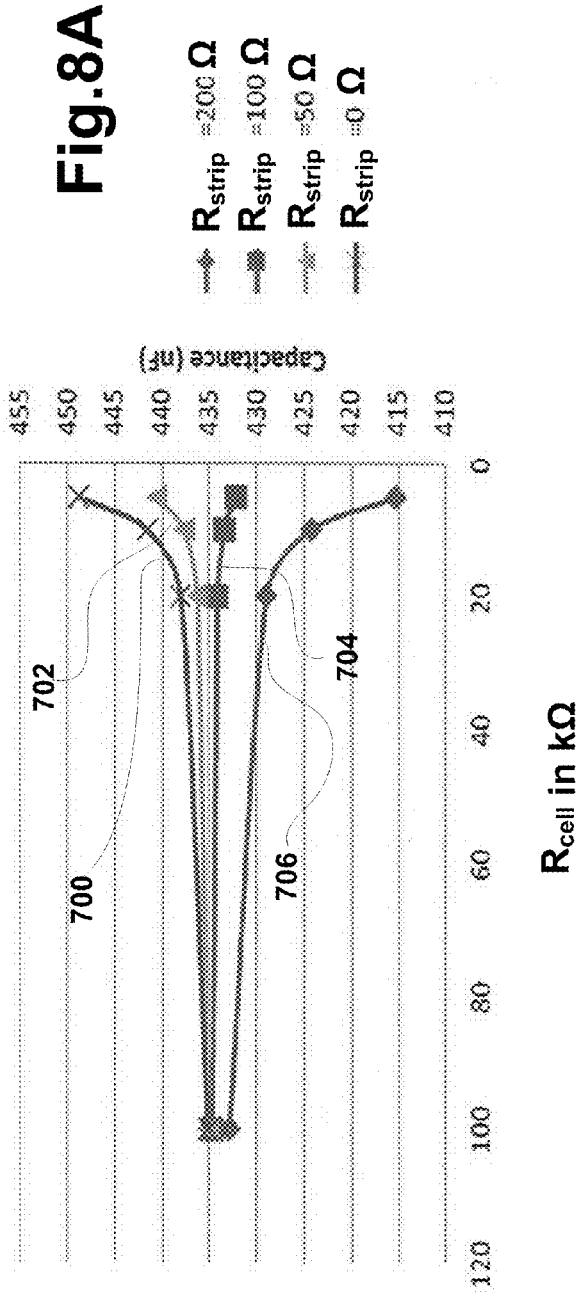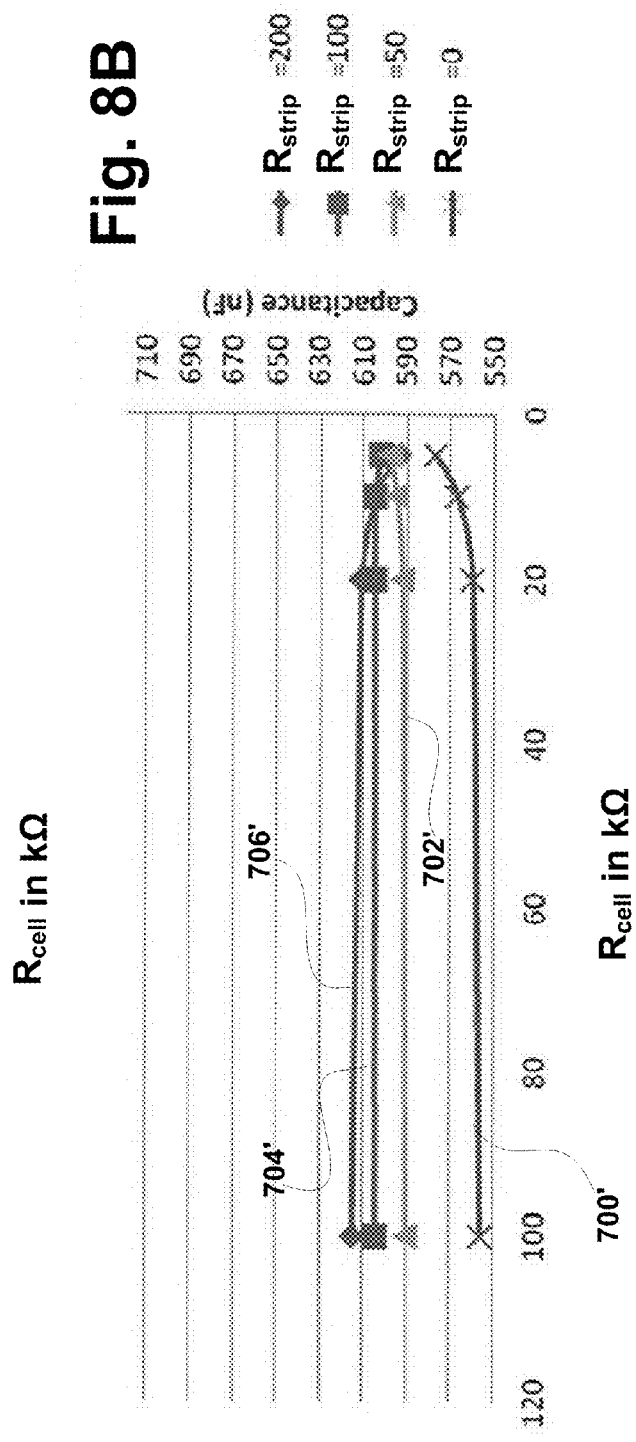

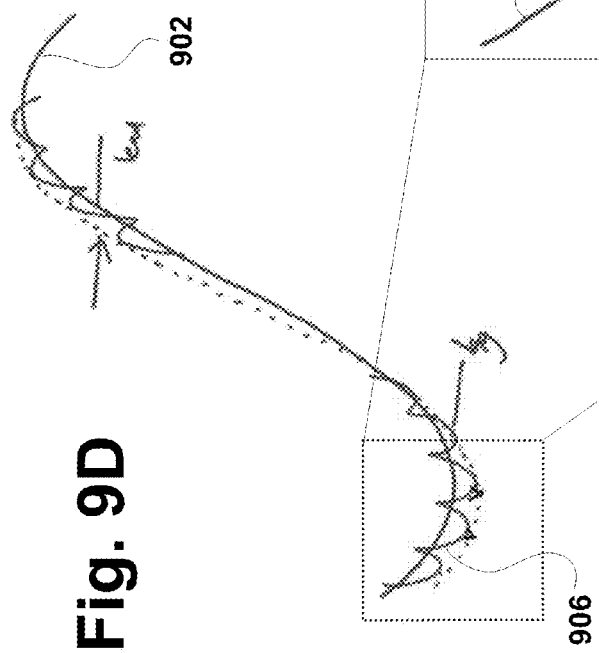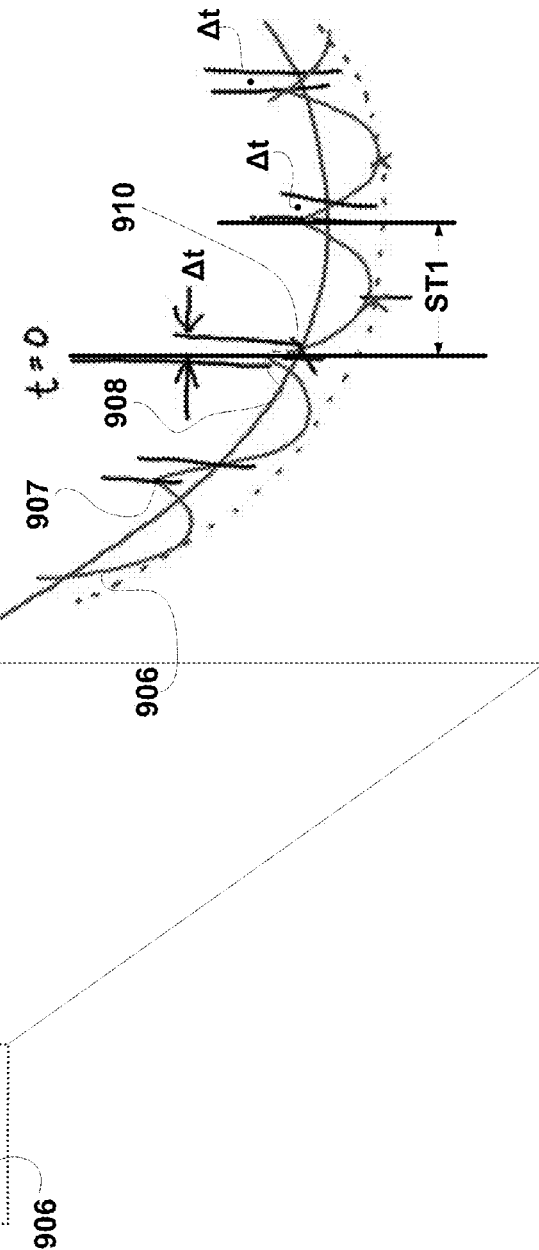

CAPACITANCE DETECTION IN ELECTROCHEMICAL ASSAY WITH IMPROVED SAMPLING TIME OFFSET

PRIORITY

This application claims the benefit of priority under 35 USC §120 as a continuation in part of prior filed application Ser. No. 13/034,281 filed on Feb. 24, 2011 and International Patent Application PCT/GB2011/000267 filed Feb. 25, 2011, both of which claim priority to U.S. Provisional Patent Application Ser. No. 61/308,167 filed Feb. 25, 2010 all of the applications are hereby incorporated by reference in their entireties herein this application.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving test cell in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. For example, variations in temperatures can affect the results of the method. This is especially relevant when the method is carried out in an uncontrolled environment, as is often the case in home applications or in third world countries. Errors can also occur when the sample size is insufficient to get an accurate result. Partially filled test strips can potentially give an inaccurate result because the measured test currents are proportional to the area of the working electrode that is wetted with sample. Thus, partially filled test strips can under certain conditions provide a glucose concentration that is negatively biased.

To alleviate some of these problems, biosensor researchers have turned to using capacitance of the test chamber to determine the fill sufficiency of the test chamber. Examples are shown and described in U.S. Pat. Nos. 6,856,125; 6,872,298; 7,195,704; and 7,199,594, all of which are hereby incorporated by reference into this application.

SUMMARY OF THE DISCLOSURE

Applicant believes that effects of parallel strip resistance in determining filled biosensor test strips have been ignored, leading to inaccurate high measurement of capacitance in a test strip, especially when lower parallel resistance is encountered. Exemplary embodiments of applicant's invention take into consideration this effect and at the same time obviate the need to determine the resistance in a biosensor electrochemical test cell.

In one aspect, a method of determining capacitance of an electrochemical biosensor test cell of a test strip is provided. The test chamber has at least two electrodes disposed in the chamber and coupled to a microcontroller. The method can be achieved by: initiating an electrochemical reaction of a sample upon deposition of the sample in the biosensor chamber; applying an oscillating signal of a predetermined frequency to the chamber; ascertaining a first sampling-time interval for measurement of an output signal based on a predetermined sampling rate per cycle of the output signal at the predetermined frequency; sampling the output signal from the chamber at a second sampling-time interval different than the first sampling-time interval such that a magnitude of each sampled output signal is measured at each succession of the second sampling-time interval instead of at the first time interval; determining a phase angle between an output signal and the oscillating input signal from the chamber based on the sampled output signal of the sampling step; and calculating a capacitance of the chamber from the phase angle. In a variation of this aspect, the second sampling-time interval is based on a predetermined offset time with respect to the first sampling-time interval, or the first sampling-time interval comprises a duration between each step change in magnitude of the output signal; and the offset time comprises a percentage of the first sampling-time interval, which the percentage comprises a range from about 5% to about 30% of the first sampling-time interval. In another variation of this aspect, the ascertaining may include: determining a duration for one wave of the signal at the predetermined frequency; dividing the duration over a number of measurement samples for each wave to obtain a time duration; and setting the first sampling-time interval as being generally equal to the time duration. In yet a further variation, the ascertaining may include evaluating the output signal to determine a time duration between each step change of the output signal; and setting the first sampling-time interval as being generally equal to the time duration. It is further noted that in this aspect, the offset time may include a percentage of the first sampling-time interval, which the percentage may range from about 5% to about 30% of the first sampling-time interval. In yet a variation of this aspect, the calculating may include calculating capacitance with a phase angle compensation to account for phase shift in a circuit used to sample the output signal. In particular, the calculating may include calculating capacitance with an equation of the form:

$$C = |i_T \sin(\Phi + \Phi_{COMP})|/2\pi fV$$

where:
C≈capacitance;
$i_T$≈total current;
Φ≈phase angle between total current and resistor current;
$\Phi_{COMP}$≈phase angle compensation;
f≈frequency; and
V≈voltage.

In another variation, the phase angle compensation may include any value from about 3 degrees to about 20 degrees. In a more particular variation, the phase angle compensation may include about 11 degrees. It is noted that in a further variation, the calculating may include: sampling a plurality of current outputs from the chamber over one cycle of the frequency; obtaining a mean of sampled current output; subtracting the mean from each sampled current of the plurality of current outputs; and extracting root-mean-squared value of all negative values from the subtracting to provide for the total current output. Alternatively, the calculating may include determining from the sampling, at least one cross-over point of the current from negative to positive values; and interpolating proximate the at least one cross-over point of the current to determine a first angle at which the current changes from positive to negative or negative to positive. It is further noted that the interpolating the at least one cross-over point of the current may include interpolating another cross-over point from the sampling to determine another angle at which the current changes from positive to negative or negative to positive; and subtracting from the another angle approximately 180 degrees to provide for a second angle. The subtracting further may include calculating an average of the first and second angles. The calculating may include determining a difference in the angle between the oscillating input current and the output current as the phase angle.

In another aspect, an analyte measurement system is provided that includes an analyte test strip and an analyte meter. The analyte test strip includes a substrate having a reagent disposed thereon and at least two electrodes proximate the reagent a in test chamber of the test strip. The analyte meter includes a strip port connector disposed to connect to the two electrodes, a power supply, and a microcontroller electrically coupled to the strip port connector and the power supply. The microcontroller is programmed to: initiate an electrochemical reaction in the biosensor chamber; apply an oscillating voltage of a predetermined frequency to the chamber; ascertain a first sampling-time interval for measurement of an output signal based on a predetermined sampling rate per cycle of the output signal at the predetermined frequency; sample the output signal from the chamber at a second sampling-time interval different than the first sampling-time interval such that a magnitude of each sampled output signal is measured at each succession of the second sampling-time interval instead of at the first time interval; determine a phase angle between a current output and the oscillating voltage from the chamber based on the sampled output signal; and calculate a capacitance of the chamber based on the determined phase angle. In this system, the second sampling-time interval is based on a predetermined offset time with respect to the first sampling-time interval. Additionally, the first sampling-time interval may include a duration between each step change in magnitude of the output signal. Specifically, the offset time may include a percentage of the first sampling-time interval; and the percentage may have a range from about 5% to about 30% of the first sampling-time interval.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 3A illustrates an exploded perspective view of the test strip of FIG. 1.

FIG. 3B illustrates a schematic electrical model of the test chamber 61 and a phasor diagram of the resistor-capacitive model.

FIG. 6A illustrates a sampling of the current output indicated at area 602.

FIG. 6B illustrates the alternating current output once the direct-current component has been removed from the sampled data of FIG. 6A.

FIGS. 6C and 6D illustrate the phase angle between the alternating voltage applied to the test strip and the alternating current output from the test strip.

FIG. 6E illustrates an interpolation of the sampled data to determine the cross-over point of FIG. 6D for comparison with the cross-over point of the applied current of FIG. 6C.

FIG. 8A illustrates referential output responses in terms of test cell resistance and test cell capacitance in a referential model of the test strip of FIG. 7B.

FIG. 8B illustrates actual output responses in terms of test cell resistance and test cell capacitance in an actual test strip.

FIGS. 9D and 9E illustrate in detail the error caused by the step change in the piecewise or stepwise output signal 906 as compared to a smooth output signal 902.

MODES OF CARRYING OUT THE INVENTION

Figure 1:
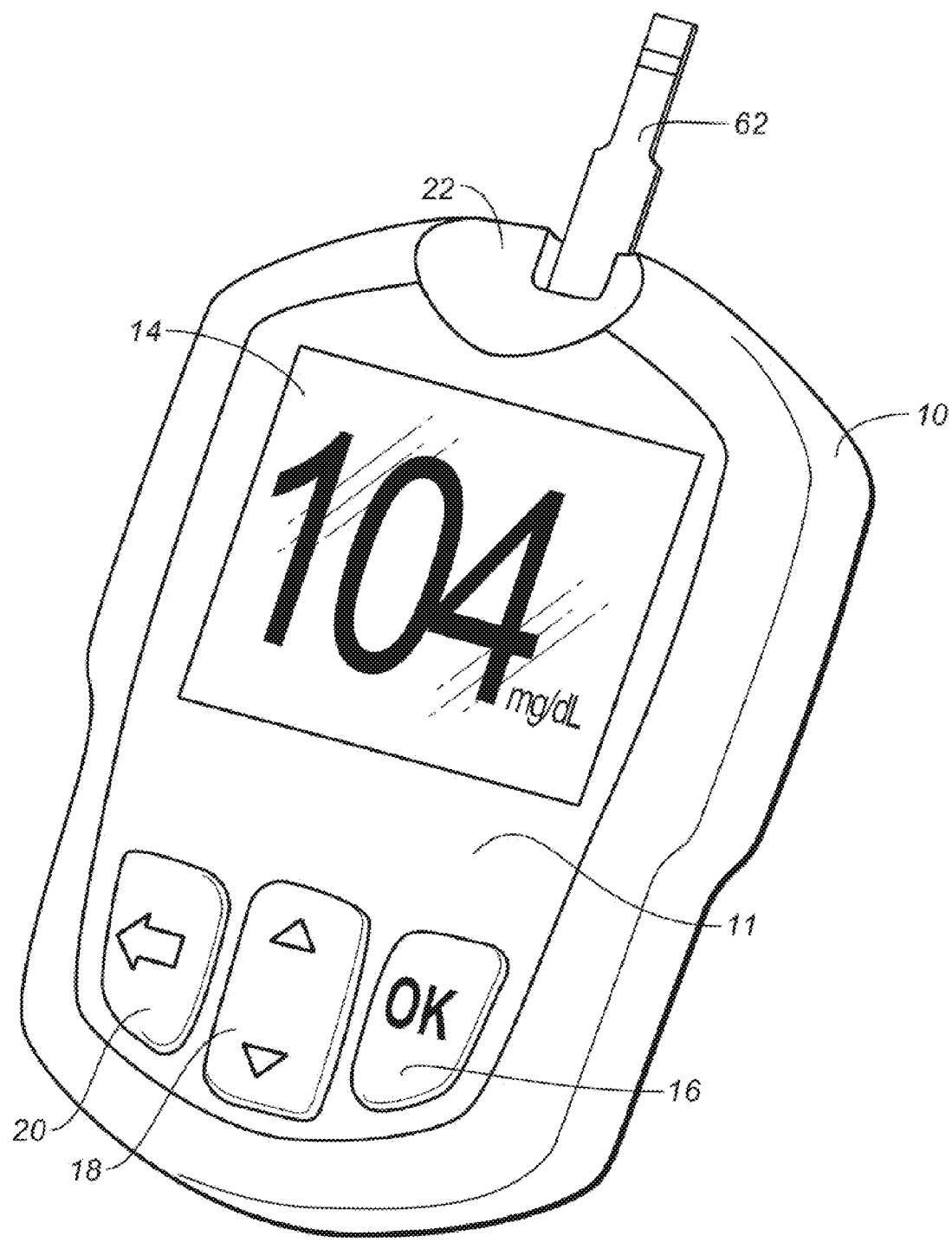
FIG. 1 illustrates an exemplary analyte measurement system including an analyte test meter and test strip.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

The subject systems and methods are suitable for use in the determination of a wide variety of analytes in a wide variety of samples, and are particularly suited for use in the determination of analytes in whole blood, plasma, serum, interstitial fluid, or derivatives thereof. In an exemplary embodiment, a glucose test system based on a thin-layer cell design with opposing electrodes and tri-pulse electrochemical detection that is fast (e.g., about 5 second analysis time), requires a small sample (e.g., about 0.4 µL (microliter)), and can provide improved reliability and accuracy of blood glucose measurements. In the reaction cell, glucose in the sample can be oxidized to gluconolactone using glucose dehydrogenase and an electrochemically active mediator can be used to shuttle electrons from the enzyme to a working electrode. A potentiostat can be utilized to apply a tri-pulse potential waveform to the working and counter electrodes, resulting in test current transients used to calculate the glucose concentration. Further, additional information gained from the test current transients may be used to discriminate between sample matrices and correct for variability in blood samples due to hematocrit, temperature variation, electrochemically active components, and identify possible system errors.

The subject methods can be used, in principle, with any type of electrochemical cell having spaced apart first and second electrodes and a reagent layer. For example, an electrochemical cell can be in the form of a test strip. In one aspect, the test strip may include two opposing electrodes separated by a thin spacer for defining a sample-receiving test cell or zone in which a reagent layer is located. One skilled in the art will appreciate that other types of test strips, including, for example, test strips with co-planar electrodes may also be used with the methods described herein.

FIG. 1 illustrates a diabetes management system that includes a diabetes data management unit 10 and a biosensor in the form of a glucose test strip 80. Note that the diabetes data management unit (DMU) may be referred to as an analyte measurement and management unit, a glucose meter, a meter, and an analyte measurement device. In an embodiment, the DMU may be combined with an insulin delivery device, an additional analyte testing device, and a drug delivery device. The DMU may be connected to the computer 26 or server 70 via a cable or a suitable wireless technology such as, for example, GSM, CDMA, BlueTooth, WiFi and the like.

Referring back to FIG. 1, glucose meter 10 can include a housing 11, user interface buttons (16, 18, and 20), a display 14, and a strip port opening 22. User interface buttons (16, 18, and 20) can be configured to allow the entry of data, navigation of menus, and execution of commands. User interface button 18 can be in the form of a two way toggle switch. Data can include values representative of analyte concentration, and/or information, which are related to the everyday lifestyle of an individual. Information, which is related to the everyday lifestyle, can include food intake, medication use, occurrence of health check-ups, and general health condition and exercise levels of an individual.

Figure 2:
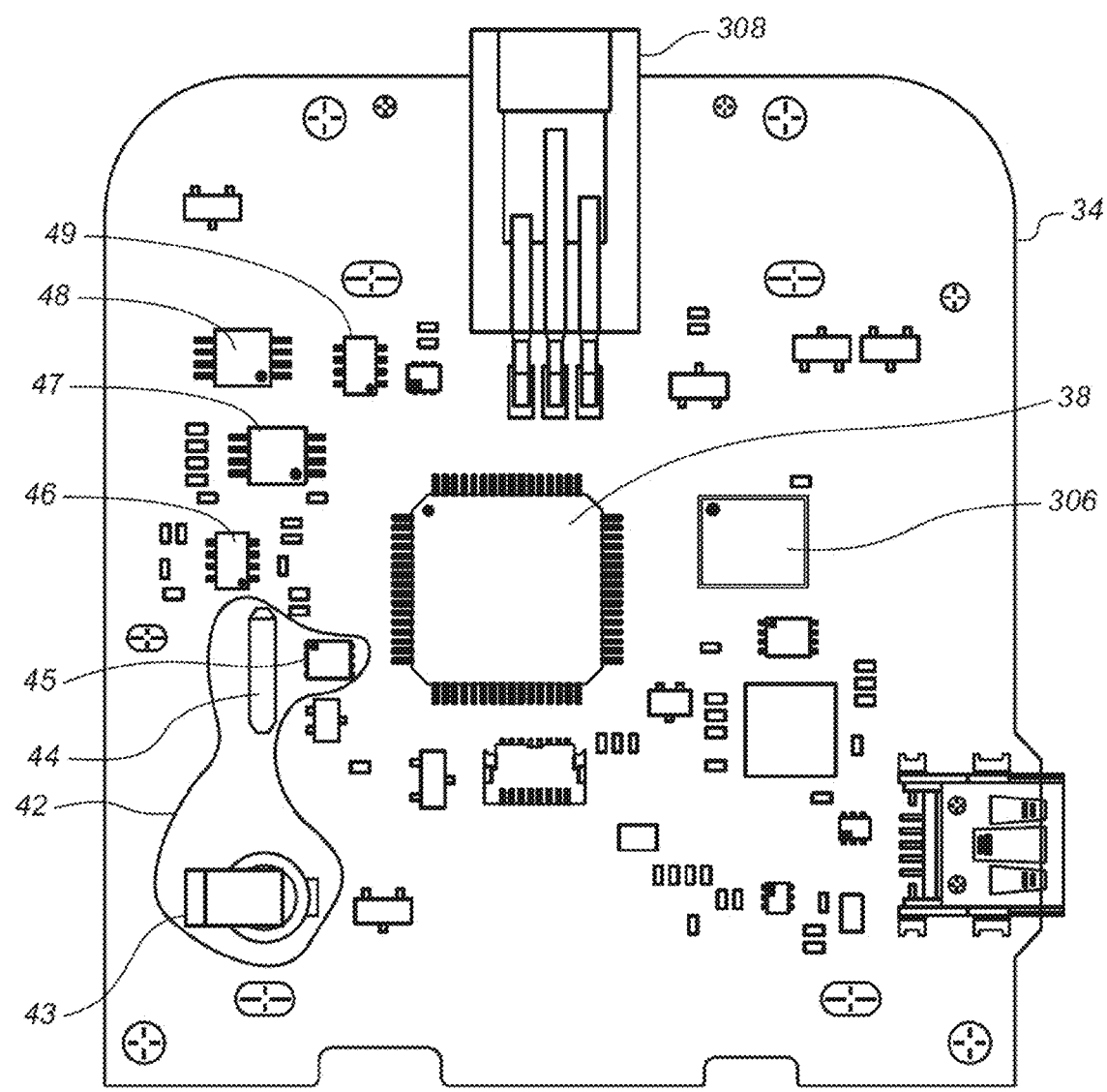
FIG. 2 illustrates in simplified schematic view of an exemplary circuit board for the meter of FIG. 1.

The electronic components of meter 10 can be disposed on a circuit board 34 that is within housing 11. FIG. 2 illustrates (in simplified schematic form) the electronic components disposed on a top surface of circuit board 34. On the top surface, the electronic components may include a strip port opening 308, a microcontroller 38, a non-volatile flash memory 306, a data port 13, a real time clock 42, and a plurality of operational amplifiers (46-49). On the bottom surface, the electronic components may include a plurality of analog switches, a backlight driver, and an electrically erasable programmable read-only memory (EEPROM, not shown). Microcontroller 38 can be electrically connected to strip port opening 308, non-volatile flash memory 306, data port 13, real time clock 42, the plurality of operational amplifiers (46-49), the plurality of analog switches, the backlight driver, and the EEPROM.

Referring back to FIG. 2, the plurality of operational amplifiers can include gain stage operational amplifiers (46 and 47), a trans-impedance operational amplifier 48, and a bias driver operational amplifier 49. The plurality of operational amplifiers can be configured to provide a portion of the potentiostat function and the current measurement function. The potentiostat function can refer to the application of a test voltage between at least two electrodes of a test strip. The current function can refer to the measurement of a test current resulting from the applied test voltage. The current measurement may be performed with a current-to-voltage converter. Microcontroller 38 can be in the form of a mixed signal microprocessor (MSP) such as, for example, the Texas Instrument MSP 430. The MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit (ASIC).

Strip port connector 308 can be located proximate the strip port opening 22 and configured to form an electrical connection to the test strip. Display 14 can be in the form of a liquid crystal display for reporting measured glucose levels, and for facilitating entry of lifestyle related information. Display 14 can optionally include a backlight. Data port 13 can accept a suitable connector attached to a connecting lead, thereby allowing glucose meter 10 to be linked to an external device such as a personal computer. Data port 13 can be any port that allows for transmission of data such as, for example, a serial, USB, or a parallel port.

Real time clock 42 can be configured to keep current time related to the geographic region in which the user is located and also for measuring time. Real time clock 42 may include a clock circuit 45, a crystal 44, and a super capacitor 43. The DMU can be configured to be electrically connected to a power supply such as, for example, a battery. The super capacitor 43 can be configured to provide power for a prolonged period of time to power real time clock 42 in case there is an interruption in the power supply. Thus, when a battery discharges or is replaced, real time clock does not have to be re-set by the user to a proper time. The use of real time clock 42 with super capacitor 43 can mitigate the risk that a user may re-set real time clock 42 incorrectly.

FIG. 3A illustrates an exemplary test strip 80, which includes an elongate body extending from a distal end 80 to a proximal end 82, and having lateral edges. As shown here, the test strip 80 also includes a first electrode layer 66a, insulation layer 66b, a second electrode layer 64a, insulation layer 64b, and a spacer 60 sandwiched in between the two electrode layers 64a and 66a. The first electrode layer 66a can include a first electrode 67a, a first connection track 76, and a first contact pad 47, where the first connection track 76 electrically connects the first electrode layer 66a to the first contact pad

Figure 4:
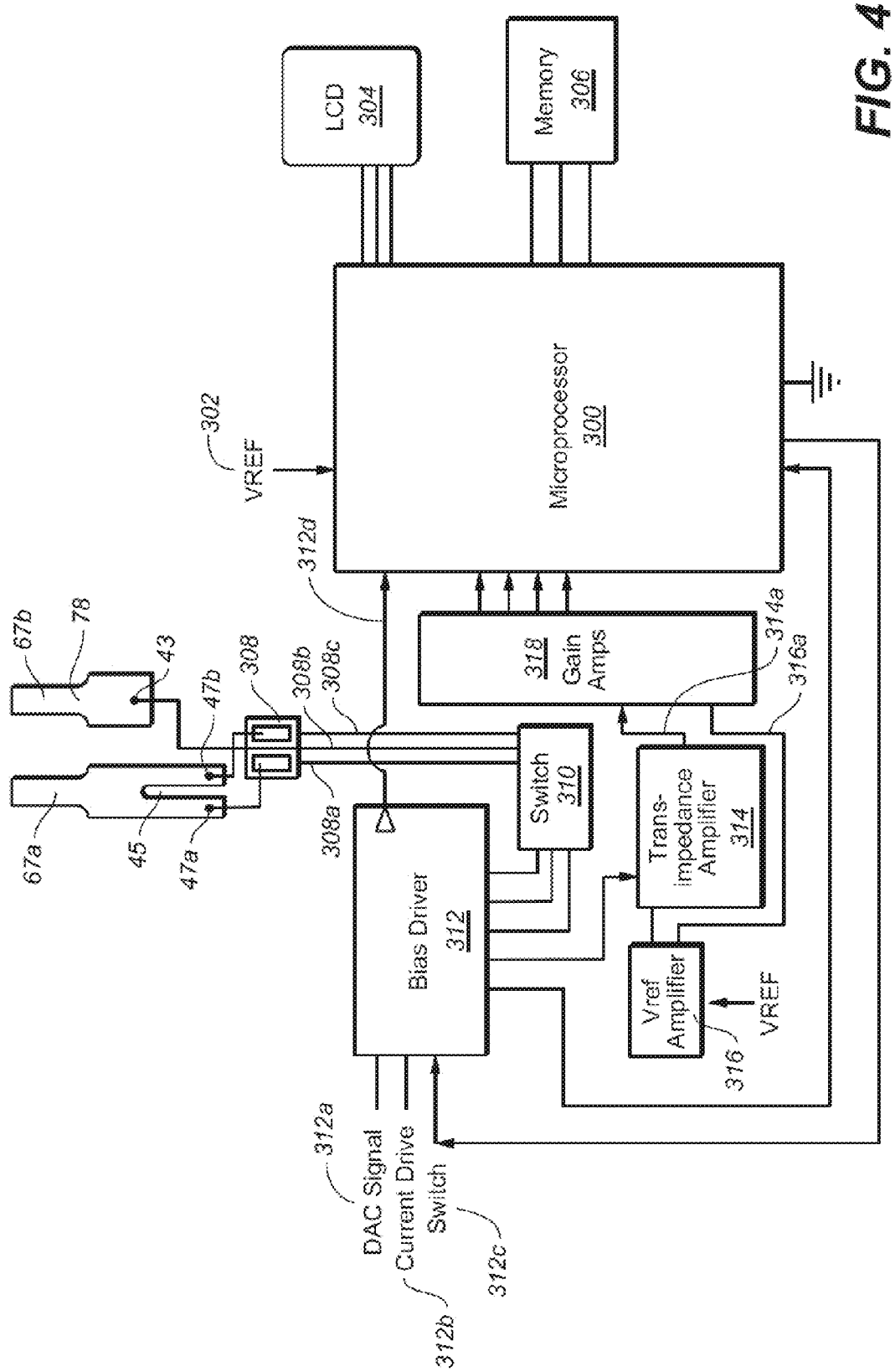
FIG. 4 illustrates a simplified schematic of the components to determine capacitance of a filled test strip.

67, as shown in FIGS. 3A and 4. Note that the first electrode 67a is a portion of the first electrode layer 66a that is immediately underneath the reagent layer 72. Similarly, the second electrode layer 64a can include a second electrode 67b, a second connection track 78, and a second contact pad 78, where the second connection track 78 electrically connects the second electrode 67b with the second contact pad 78, as shown in FIGS. 3 and 4. Note that the second electrode includes a portion of the second electrode layer 64a that is above the reagent layer 72.

As shown in FIG. 3A, the sample-receiving electrochemical test cell 61 is defined by the first electrode 67a, the second electrode 67b, and the spacer 60 near the distal end 80 of the test strip 80. The first electrode 67a and the second electrode 67b can define the bottom and the top of sample-receiving electrochemical test cell 61, respectively. A cutout area 68 of the spacer 60 can define the sidewalls of the sample-receiving electrochemical test cell 61. In one aspect, the sample-receiving electrochemical test cell 61 can include ports 70 that provide a sample inlet and/or a vent. For example, one of the ports can allow a fluid sample to ingress and the other port can allow air to egress. In one exemplary embodiment, the first electrode layer 66a and the second electrode layer 64a can be made from sputtered palladium and sputtered gold, respectively. Suitable materials that can be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated.

Referring back to FIG. 3A, the area of first electrode and second electrode can be defined by the two lateral edges and cutout area 68. Note that the area can be defined as the surface of the electrode layer that is wetted by liquid sample. In an embodiment, the adhesive portion of spacer 60 can intermingle and/or partially dissolve the reagent layer so that the adhesive forms a bond to the first electrode layer 66A. Such an adhesive bond helps define the portion of the electrode layer that can be wetted by liquid sample and also electrooxidize or electroreduce mediator.

Either the first electrode or the second electrode can perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it can be oxidized at the first electrode as long as the test voltage is sufficiently less than the redox mediator potential with respect to the second electrode. In such a situation, the first electrode performs the function of the working electrode and the second electrode performs the function of a counter/reference electrode. Note that one skilled in the art may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term bulk solution refers to a portion of the solution sufficiently far away from the working electrode where the reduced mediator is not located within a depletion zone. It should be noted that unless otherwise stated for test strip 80, all potentials applied by test meter 10 will hereinafter be stated with respect to second electrode. Similarly, if the test voltage is sufficiently greater than the redox mediator potential, then the reduced mediator can be oxidized at the second electrode as a limiting current. In such a situation, the second electrode performs the function of the working electrode and the first electrode performs the function of the counter/reference electrode. Details regarding the exemplary test strip, operation of the strip and the test meter are found in U.S. Patent Application Publication No. 20090301899, which is incorporated by reference in its entirety herein.

Referring to FIG. 3A, test strip 80 can include one or more working electrodes and a counter electrode. Test strip 80 can also include a plurality of electrical contact pads, where each electrode can be in electrical communication with at least one electrical contact pad. Strip port connector 308 can be configured to electrically interface to the electrical contact pads and form electrical communication with the electrodes. Test strip 80 can include a reagent layer that is disposed over at least one electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then measure a concentration of the reduced mediator in the form of a current. In turn, glucose meter 10 can convert the current magnitude into a glucose concentration. Details of the preferred test strip are provided in U.S. Pat. Nos. 6,179,979; 6,193,873; 6,284,125; 6,413,410; 6,475,372; 6,716,577; 6,749,887; 6,863,801; 6,890,421; 7,045,046; 7,291,256; 7,498,132, all of which are incorporated by reference in their entireties herein.

FIG. 4 illustrates, in simplified schematic form, of various functional components utilized for capacitance determination. In particular, the components include a microcontroller 300. A preferred embodiment of the microcontroller 300 is available from Texas Instrument as ultra-low power microcontroller model MSP430. Microcontroller ("MC") 300 may be provided with DAC output and built-in A-D conversion. MC 300 is suitably connected to a LCD screen 304 to provide a display of the test results or other information related to the test results. Memory 306 is electrically connected to the MC 300 for storage of test results, sensed current and other necessary information or data. The test strip may be coupled for a test measurement via a strip port connector ("SPC") 308. SPC 308 allows the test strip to interface with MC 300 via a first contact pad 47a, 47b and a second contact pad 43. The second contact pad 43 can be used to establish an electrical connection to the test meter through a U-shaped notch 45, as illustrated in FIG. 4. SPC 308 may also be provided with electrode connectors 308a and 308c. The first contact pad 47 can include two prongs denoted as 47a and 47b. In one exemplary embodiment, the first electrode connectors 308a and 308c separately connect to prongs 47a and 47b, respectively. The second electrode connector 308b can connect to second contact pad 43. The test meter 10 can measure the resistance or electrical continuity between the prongs 47a and 47b to determine whether the test strip 80 is electrically connected to the test meter 10.

Referring to FIG. 4, SPC 308 is connected to switch 310. Switch 310 is connected to the bias driver 312. Bias driver 312 is provided with the DAC signal 312a; current drive 312b and switch signal 312c. The MC 300 provides the DAC signal 312a, which includes analogue voltages in the range 0 to Vref (e.g., about 2.048V). The bias driver 312 can operate in two modes—constant voltage, or constant current. The current-driver line 312b controls the mode of the bias driver 312. Setting the line 312b low converts an op-amp in the bias driver 312 to a voltage follower amplifier. DAC signal 312a output is scaled to Vref/2+/−400 mV full scale. The op-amp in the bias driver outputs this voltage directly to the MC 300 as line driver-line 312d. The voltage of line 312d is generated with respect to the Vref/2 virtual ground. So to drive a suitable bias (e.g., about 20 mV bias), the DAC must drive (through a suitable scaler) about 1.044V. To drive a bias of about +300 mV, the DAC must generally provide about 1.324V, and for the −300 mV bias, the DAC must generally provide about 0.724V. The bias driver circuit 312 also generates the 109 Hz sine wave, which is used for fill detection via capacitance measurement.

On the other hand, if current-drive signal 312a to bias driver 312 is held high, the DAC output is scaled to approximately 0 to approximately 60 mV full scale. Switch signal 312c may also be energized, causing the current path through the test strip to be diverted through a resistor in bias driver 312. The op-amp in bias driver 312 attempts to control the voltage drop across the resistor in this to be the same as the scaled DAC drive—producing in this case a current of approximately 600 nA. This current is used for sample detection in order to initiate a test measurement.

Bias driver 312 is also connected to a trans-impedance amplifier circuit ("TIA circuit") 314. TIA circuit 314 converts the current flowing though the strip's electrode layer 66a (e.g., palladium) to electrode layer 64a (e.g., gold) contacts into a voltage. The overall gain is controlled by a resistor in TIA circuit 314. Because the strip 80 is a highly capacitive load, normal low-offset amplifiers tend to oscillate. For this reason a low-cost op-amp is provided in the TIA circuit 314 as a unity gain buffer and incorporated within the overall feedback loop. As a functional block, circuit 314 acts as dual op-amp system with both high drive capability and low voltage offset. The TIA circuit 314 also utilizes a virtual ground (or virtual earth) to generate the 1.024V bias on the electrode layer 64a (e.g., gold) contact of the SPC 308. Circuit 314 is also connected to a Vref amplifier circuit 316. This circuit, when in current measuring mode, uses a virtual ground rail set at Vref/2 (approximately 1.024V), allowing both positive and negative currents to be measured. This voltage feeds all of the gain amplifier stage 318. To prevent any circuit loads from 'pulling' this voltage, a unity gain buffer amplifier may be utilized within the Vref amplifier circuit 316.

The strip current signal 314a from the TIA circuit 314 and the virtual ground rail 316a (~Vref/2) from the voltage reference amplifier 316 are scaled up as needed for various stages of the test measurement cycle. In the exemplary embodiment, MC 300 is provided with four channels of amplified signal sensed from the test strip with varying amplifications of the sensed current as need for different stages of the measurement cycle of the test strip during an analyte assay.

In one embodiment, the test meter 10 can apply a test voltage and/or a current between the first contact pad 47 and the second contact pad 43 of the test strip 80. Once the test meter 10 recognizes that the strip 80 has been inserted, the test meter 10 turns on and initiates a fluid detection mode. In one embodiment, the meter attempts to drive a small current (e.g. 0.2 to 1 µA) through the strip 80. When there is no sample present the resistance is greater than several Mega Ohms, the driving voltage on the op-amp trying to apply the current goes to the rail. When a sample is introduced the resistance drops precipitously and the driving voltage follows. When the driving voltage drops below a pre-determined threshold the test sequence is initiated.

Figure 5A:
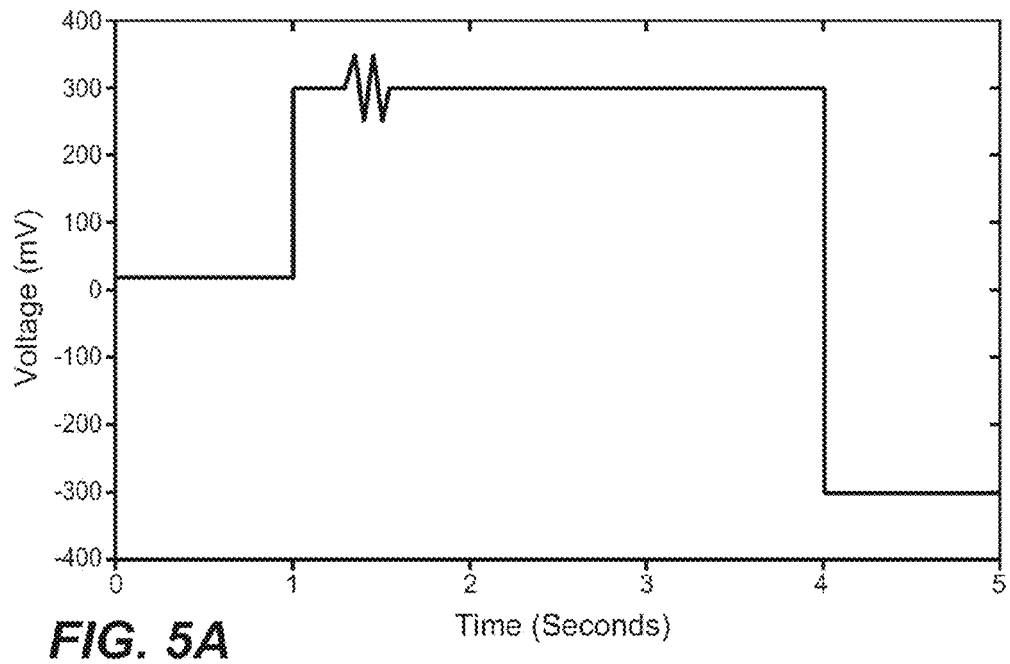
FIG. 5A illustrates the application of voltage over time applied to the test strip.

FIG. 5A shows the voltage to be applied between the electrodes. Time zero is taken to be when the sample detection method has detected that a sample first begins to fill the strip. Note that the sine wave component shown at approximately 1.3 seconds in FIG. 5A is not drawn on the correct timescale for illustration purposes.

After a sample has been detected in the test strip chamber 61, the voltage between the strip electrodes is stepped to a suitable voltage in millivolts of magnitude and maintained for a set amount of time, e.g., about 1 second, then stepped to a higher voltage and held for a fixed amount of time, then a sine wave voltage is applied on top of the DC voltage for a set amount of time, then the DC voltage is applied for a further amount of time, then reversed to a negative voltage and held for a set amount of time. The voltage is then disconnected from the strip. This series of applied voltages generates a current transient such as the one shown in FIG. 5B.

Figure 5B:
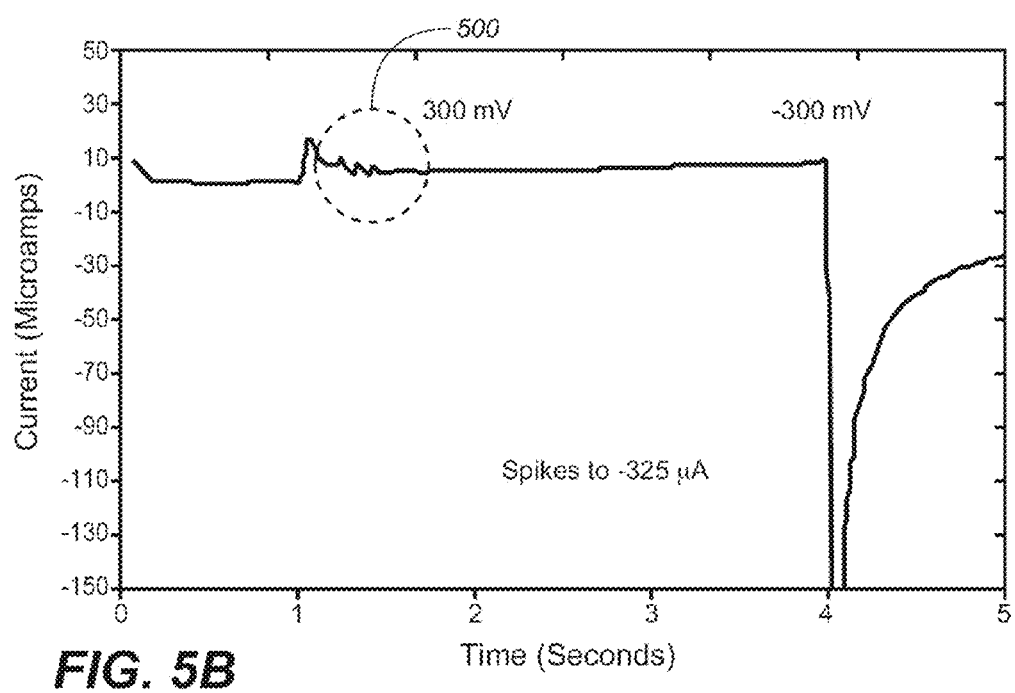
FIG. 5B illustrates the amplitude of the current output response from the test strip over time.

In FIG. 5B, the current signal from about 0 to about 1 second (as well as later current samples) may be used for error checking and to distinguish a control solution sample from a blood sample. The signal from about 1 to about 5 seconds is analyzed to obtain a glucose result. The signal during this period is also analyzed for various errors. The signal from about 1.3 to 1.4 seconds is used to detect whether or not the sensor is completely filled with sample. The current from 1.3 to 1.32 seconds, denoted here as trace 500, is sampled at approximately 150 microsecond intervals to determine whether sufficient volume of physiological fluid has filled chamber 61 of the test strip.

In one embodiment for performing a sufficient volume check, a capacitance measurement is used to infer sufficient analyte fill of the chamber 61 of the test strip 80. A magnitude of the capacitance can be proportional to the area of an electrode that has been coated with sample fluid. Once the magnitude of the capacitance is measured, if the value is greater than a threshold and thus the test strip has a sufficient volume of liquid for an accurate measurement, a glucose concentration can be outputted. But if the value is not greater than a threshold, indicating that the test strip has insufficient volume of liquid for an accurate measurement, and then an error message can be outputted.

After a sample has been detected in the test strip electrochemical test cell 61, the voltage between the strip electrodes is stepped to a suitable voltage in millivolts of magnitude and maintained for a set amount of time, e.g., about 1 second, then stepped to a higher voltage and held for a fixed amount of time, then a sine wave voltage is applied on top of the DC voltage for a set amount of time, then the DC voltage is applied for a further amount of time, then reversed to a negative voltage and held for a set amount of time. The voltage is then disconnected from the strip. This series of applied voltages generates a current transient such as the one shown in FIG. 5B.

In one method for measuring capacitance, a test voltage having a constant component and an oscillating component is applied to the test strip. In such an instance, the resulting test current can be mathematically processed, as described in further detail below, to determine a capacitance value.

Applicant believes that the biosensor test chamber 61 with the electrode layers can be modeled in the form of a circuit having a parallel resistor and capacitor as shown in FIG. 3B.

In this model of FIG. 3B, R represents the resistance encountered by the current and C represents a capacitance resulting from the combination of the physiological fluid and reagent electrically coupled to the electrodes. To initiate a determination of capacitance of the chamber, an alternating bias voltage may be applied across the respective electrodes disposed in the chamber, and a current from the chamber is measured. The filling of the chamber 61 is believed to be generally a measure of capacitance only and thus any parasitic resistance, such as, for example, R, must not be included in any determination or calculation of capacitance. Hence, in measuring or sensing the current, any parasitic resistance is believed to affect the measured current. Applicant, however, has discovered a technique to derive capacitance without requiring utilization or knowledge of the resistance through the chamber as modeled above. In order to further explain this technique, a short discussion of the mathematical foundation underlying the technique is warranted.

According to Kirchhoff's Law, total current ($i_T$) through the circuit of FIG. 3B is approximately the sum of the current flowing through the resistor ($i_R$) and through the capacitor ($i_C$). When an alternating voltage V (as measured as RMS) is applied, the resistor current ($i_R$) may be expressed as:

$$i_R = V/R \qquad \text{Eq. 1}$$

Capacitor current ($i_C$) can be expressed as:

$$i_c = j\omega C V \qquad \text{Eq. 2}$$

Where:
j is an imaginary number operator indicating that current leads voltage by about 90 degrees in a capacitor; and
ω is the angular frequency 2πf where f is frequency in Hertz.

The summation of these components is shown in the phasor diagram of FIG. 3B. In the phasor diagram, Φ represents the phase angle of the input as compared to the output. Phase angle Φ is determined by the following trigonometric function:

$$\tan \Phi = I_C/I_R \qquad \text{Eq. 3}$$

By Pythagoras theorem, the square of the total current $i_T$ can be calculated as:

$$i_T^2 = i_C^2 + i_R^2 \qquad \text{Eq. 4}$$

By rearranging Eq. 4 and substituting Eq. 3, the following equation is arrived at:

$$i_C^2 = i_T^2 - i_C^2/(\tan \Phi)^2 \qquad \text{Eq. 5}$$

Resolving for capacitor current $i_C$ and combining with Eq. 2:

$$i_C = \sqrt{(i_T^2*(\tan \Phi)^2/((\tan \Phi)^2+1))} = \omega C V \qquad \text{Eq. 6}$$

Rearranging for C and expanding w, the capacitance becomes:

$$C = (\sqrt{(i_T^2*(\tan \Phi)^2/((\tan \Phi)^2+1))})/2\pi f V \qquad \text{Eq. 7}$$

Simplification of Eq. 7 leads to:

$$C = |(i_T \sin \Phi)|/2\pi f V \qquad \text{Eq. 8}$$

It can be seen that Eq. 8 does not reference to the resistor current. Consequently, if the system can drive an alternating voltage with frequency f and root-mean-squared ("RMS") amplitude V, and measure total current $i_T$ as RMS value and phase angle Φ, capacitance C of the test chamber 61 can be accurately calculated without having to determine resistance in the biosensor test chamber. This is believed to be of substantial benefit because the resistance of the biosensor strip is difficult to measure, and varies over the 5 second assay time. Resistance is believed to arise from how many charge carriers can flow through the strip for a given electrical bias (voltage), and is therefore reaction dependent. At the 1.3 second point in the assay, the resistance is expected to be anything from 10 kΩ to perhaps 100 kΩ. Hence, by not having to determine the resistance in the biosensor chamber or even the resistance in the measuring circuit, such as a sensor resistor, applicant's invention have advanced the state of the art in improving of the entire test strip.

Implementation of an exemplary technique to determine capacitance C based on Eq. 8 can be understood in relation FIGS. 6A, 6B, 6C, 6D, 6E, and 7. As illustrated in FIG. 5A and FIG. 7, an AC test voltage (±50 mV peak-to-peak) of approximately 109 Hz can be applied for 2 cycles during approximately 1-1.3 seconds or at least one cycle. In the preferred embodiments, the first cycle can be used as a conditioning pulse and the second cycle can be used to determine the capacitance. The alternating test voltage can be of a suitable waveform, such as, for example, a sine wave of approximately 109 Hertz with approximately 50 millivolts peak (FIG. 6C). The sampling can be of any suitable sampling size per cycle, such as, for example approximately 64-65 samples per cycle, shown here in FIG. 6A. Hence, each sample represents approximately 5.6 degrees of the exemplary sine wave.

In FIG. 6A, the system adds a direct-current voltage offset to the alternating current bias and therefore the measured samples in FIG. 6A will also have a direct-current offset, which must be removed via steps 706 and 708 in order to determine the total current $i_T$ according to one example of applicant's technique.

In this technique, a mean of all the 64-65 samples, referenced here as 602, in FIG. 6A is derived, which will provide a threshold for the zero current of the AC component of the samples. A benefit of this derivation is that the noise across the samples is averaged out. For each sample point, the mean value is subtracted out of each sampled point, which results in isolating the alternating current component, shown here in FIG. 6B. Thereafter, a RMS value of all the negative values is taken to provide for a substantially accurate magnitude of the total current $i_T$. It is noted that the RMS value of the positive values could also be taken, but applicant believes that the positive values are disjointed due to being split across the first and fourth quadrants of the overall cycle, and therefore the negative values are preferred. Once the samples 602 have been manipulated to remove the DC offset, the samples can be plotted to show the output of the current over time, as referenced here at 604 in FIG. 6B.

To determine the phase angle, the system or processor 300, as appropriately programmed can compare the oscillating input voltage, shown here in FIG. 6C to the oscillating output current to determine the phase angle. In the preferred embodiments, the sampled data 604 is analyzed to determine a crossover point from positive to negative current. Because the sampling is based on a discrete number of samples, interpolation can be used to determine substantially when the output current crosses over the zero current line. In the embodiment described here, the phase angle Φ is less than 90 degrees and approximately 87 degrees. For increased accuracy, interpolation can be performed at another cross-over point with approximately 180 degrees subtracted from this second interpolated point. The two interpolated values should be within a few degrees and may be averaged out to increase accuracy.

Once the phase angle has been derived, capacitance can be calculated using Eq. 8. Once capacitance of the test strip 80 has been determined, a two-point calibration can be performed to normalize the capacitance value to a value that is independent of any tolerances of the analog components (e.g., resistors, capacitors, op-amps, switches and the like). Briefly, the two-point calibration is performed by: placing a 550 nF capacitor with 30 k parallel resistance across the measurement input; command the meter to measure the capacitance, and note the value produced; place a 800 nF capacitor with 30 k parallel resistance across the measurement input; command the meter to measure the capacitance, and note the value produced. These two points will give an indication of the gain and offset of the measurement capability of that particular hardware instance (not the design). A slope and offset are then calculated from the measurement errors, and stored in the meter's memory. The meter is now calibrated. When a strip is inserted and a sample applied, the capacitance is measured and the stored slope and offset are applied to correct the measurement.

After completion of the device calibration, an evaluation is made to determine whether the test chamber 61 has been sufficiently filled with test fluid. The evaluation can be based on a capacitance magnitude of at least 65% to 85% of an average capacitance value derived from a large sample of good filled test strips.

Figure 7A:
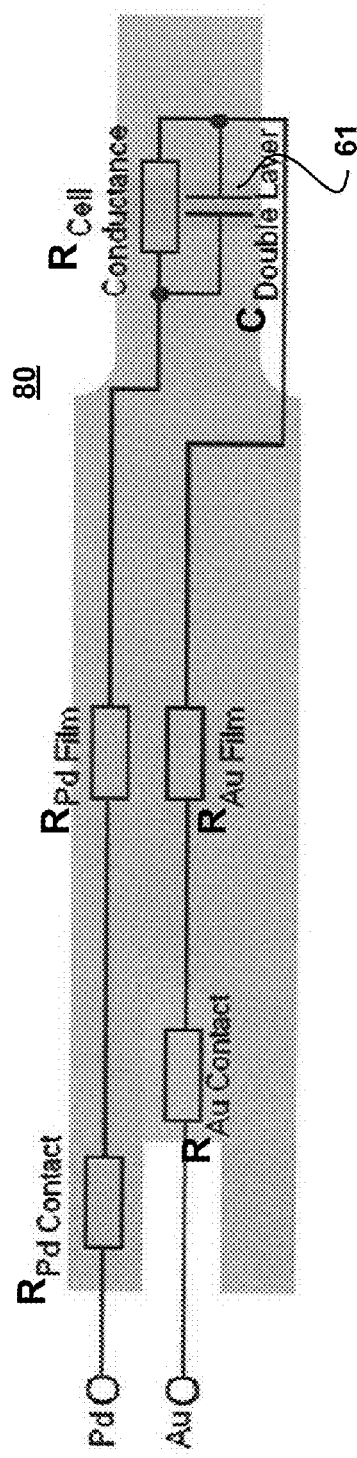
FIG. 7A illustrates an overlay of an electrical model over an outline of a strip of FIG. 3A to show various resistor sources from respective components of the test strip and capacitance of the test cell.
Figure 7C:
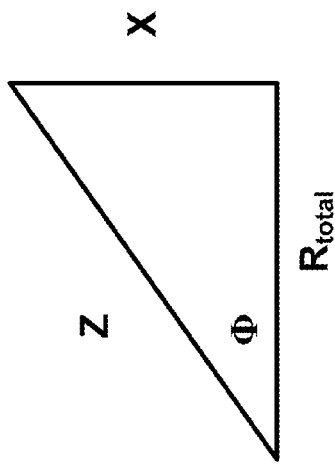
FIG. 7C illustrates a phasor diagram for the model of FIG. 7B.
Figure 7B:
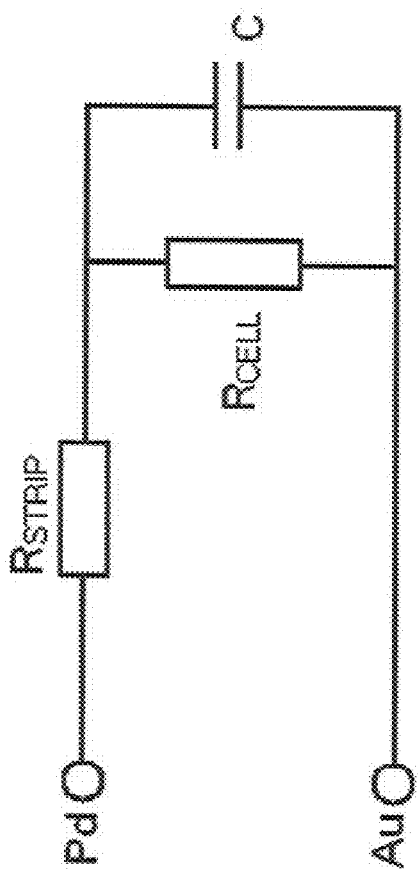
FIG. 7B illustrates an electrical schematic representation of the model of the test cell 61 and resistance of the test strip connectors.

Although the technical feature described above is believed to be sufficient for its intended use, it is believed that a more robust capacitance measurement can be made with a more comprehensive model. As such, applicant believes that the biosensor test strip 80 and test cell 61 with the electrode layers in FIG. 3A can be represented as a series of resistors $R_{Pdcontact}$, $R_{PdFilm}$, $R_{AuContact}$, and $R_{AuFilm}$ in FIG. 7A, and the test cell 61 can be represented as a parallel resistor-capacitor circuit having $R_{Cell\ Conductance}$ and $C_{DoubleLayer}$ in FIG. 7A. The resistors of the strip 80 and the parallel resistor-capacitor of test cell 61 can be modeled in the form of a circuit having a series resistor $R_{strip}$ for the strip gold and palladium layers and a parallel resistor $R_{cell}$ and capacitor C circuit for the test cell 61 as shown in FIG. 7B. In this model of FIG. 7B, the system can drive an alternating voltage with frequency f and root-mean-squared ("RMS") amplitude V, and measure total current $i_T$ as RMS value and phase angle Φ, capacitance C of the test cell 61 can be derived with the appropriate offset to account for the strip resistivity $R_{strip}$ and any phase shifting caused by the measurement circuit.

Through the use of actual measurements and mathematical modeling, the resistance of $R_{strip}$ was determined to be in the range of about 120 Ohms to about 150 Ohms (with about 135 Ohms being common) depending on the variation of the resistance of the Au and Pd contacts. It was believed that the resistance for $R_{strip}$ in the range of about 150 Ohms was negligible in comparison to the much larger impedance of $R_{cell}$ and $C_{cell}$. Hence, with the assumption that nominal value for Rcell is about 33 kilo-Ohms and $C_{cell}$ of about 600 nanoFarad at 109 Hertz, the phase angle was approximately 85.6 degrees. However, with the resistance of $R_{strip}$ (~150 Ohms) added to the cell, the measured phase angle became about 82.7 degrees, a difference of about 3.5 degrees. While small, this difference is believed to have a significant impact on the capacitance measurement. Moreover, while the trans-impedance stage 314 (FIG. 4) has virtually no phase shift associated with this stage (the phase shift being about 0.007 degrees at about 109 Hz), the gain stage 318 (FIG. 4) at about 109 Hz showed a phase shift of about 6.1 degrees nominally. This additional phase shift can be offset by introduction of a compensation value $\Phi_{COMP}$ by accounting for the phase shifts caused by $R_{strip}$ and the various stages of the circuit in FIG. 4. The compensation value $\Phi_{COMP}$ can now be applied to Equation 8 to give a more accurate capacitance measurement in Equation 9.

$$C=|i_T\sin(\Phi+\Phi_{COMP})|/2\pi fV \qquad \text{Eq. 9}$$

In the preferred embodiments, the compensation phase angle $\Phi_{COMP}$ ranges from about 3 to about 25 degrees and preferably about 11 degrees.

Figure 7D:
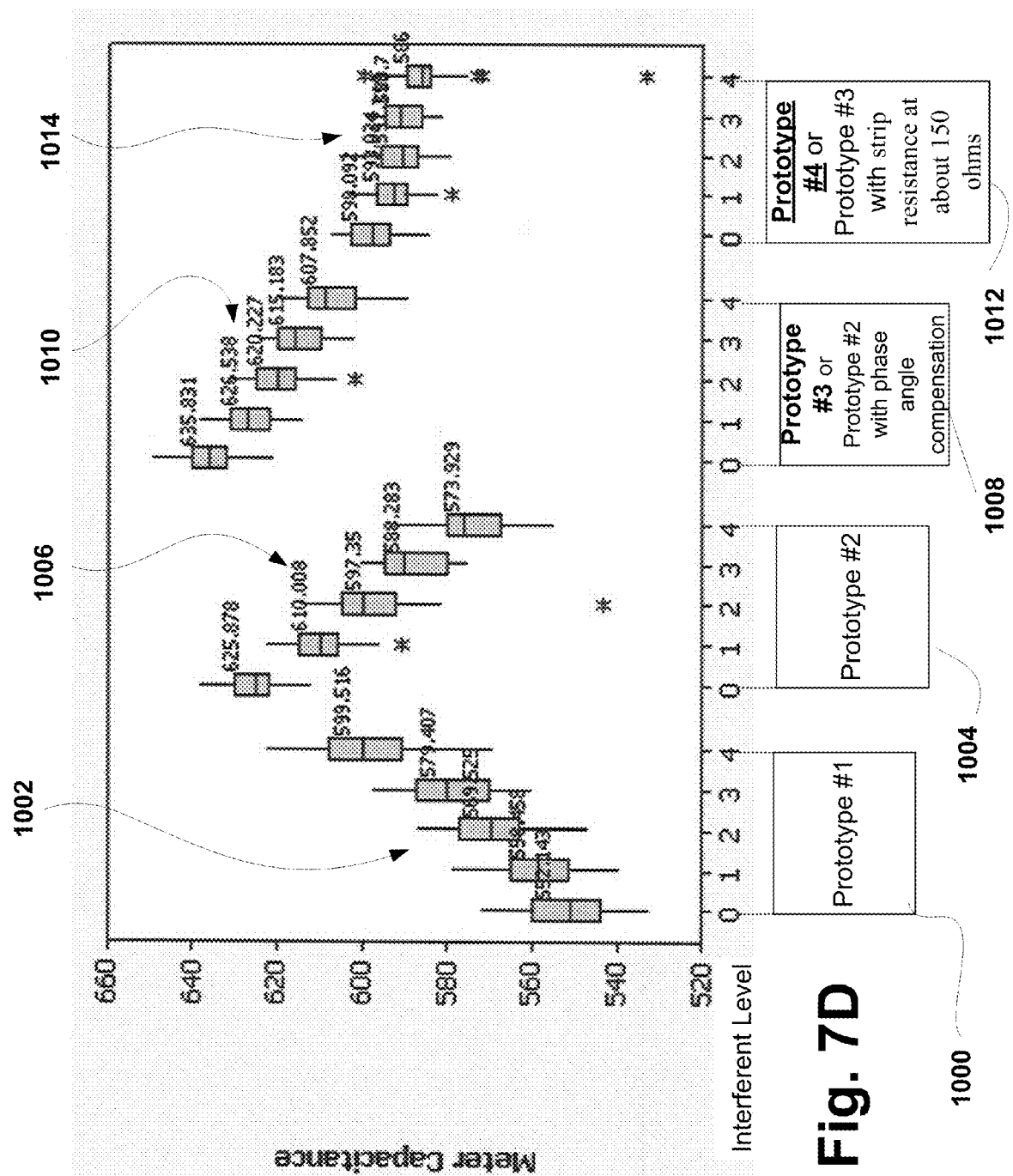
FIG. 7D illustrates the improvement for an embodiment as compared to earlier prototypes.

To demonstrate the improvements brought about by his technique above, experiments were carried out to determine the ability of the technique to determine capacitance despite increasing levels of interferants, which would normally affect the capacitance response. FIG. 7D shows the measured capacitance to varying levels of gentisic acid interference on different prototypes. Prototype #1 was a blood glucose measurement system available in the Netherlands under the trade name of Verio and utilized without any phase angle correction; Prototype #2 was a blood glucose measurement system available in France under the trade name of Verio Pro; Prototype #3 is similar to Prototype #2 but utilized with Equation 9 and along with a compensated phase angle of about 6 degrees to account for the measurement circuit; and Prototype #4 which is Prototype #3 with 11 degrees of phase angle compensation with the strip calibrated for a strip resistance Rstrip of about 150 Ohms. The numbers "0 1 2 3 4" indicates increasing levels of gentisic acid added to blood volume and saline. In particular, at the "0" level, no gentisic acid is added; at the "1" level, the concentration is about 0.45 mg per deciliter; at the "2" level, the concentration is about 0.90 mg/dL; at the "3" level, the concentration is about 1.35 mg/dL; and at the "4" level, the concentration is about 1.8 mg/dL. Parameters utilized for FIG. 7D are provided below in Table 1 where the "Test Level" is the final concentration of gentisic acid in the samples used in the experiments where level 0 means that no gentisic acid is in the sample, level 1 means about 0.45 mg of gentisic acid per deciliter of sample volume; level 2 means about 0.90 mg/dL; level 3 means about 1.35 mg/dL and level 4 means about 1.8 mg/dL, which samples include the blood volume along with the intereferant (i.e., gentisic acid) and the saline to give the 4000 microliter test samples in varying concentration.

TABLE 1

| Test Level | Blood Volume μl | Interferent Stock Solution Volume μl | Saline Volume μl |
| --- | --- | --- | --- |
| 4 (1.80 mg/dL) | 3800 | 200 | 0 |
| 3 (1.35 mg/dL) | 3800 | 150 | 50 |
| 2 (0.90 mg/dL) | 3800 | 100 | 100 |
| 1 (0.45 mg/dL) | 3800 | 50 | 150 |
| 0 (0 mg/dL) | 3800 | 0 | 200 |

Referring to FIG. 7D, applicant notes that a higher level of acidic concentration has the effect of reducing resistance of the test cell, $R_{CELL}$. For Prototype #1, the measured capacitance averaged about 552 nanoFarads without any gentisic acid in the sample. As the level of gentisic acid is added, the capacitance value increases to about 599 nanoFarads for an interval of about 47 nanoFarads. For Prototype #2, increasing the level of gentisic acid caused the capacitance magnitudes to decline from an average of about 625 nanoFarad (no gentisic acid) to about 573 nanoFarad, or an interval of about 52 nanoFarads. With phase angle compensation for the measurement circuit, Prototype #3 showed a decrease from an average of 635 nanoFarad (no gentisic acid added) to about 607 nanoFarad, or interval of about 28 nanoFarads. In contrast, with the phase angle compensation and the use of strip resistance set at about 150 ohms, Prototype #4 showed a decrease from an average of about 598 nanoFarad to about 586 nanoFarad, an interval of about 12 nanoFarads or a reduction of more than 50% from Prototype #3. Applicant note that not only is the interval between the highest average capacitance and lowest capacitance decreasing, the variation between the highest and lowest magnitude of capacitance for each level of gentisic acid (the area of each vertically oriented rectangle) is smaller from Prototype #2 to Prototype #4. These results indicate that capacitance measurements became less sensitive to various levels of interferents such as gentisic acid with the use of applicant's techniques.

The modeled circuit of FIG. 7B predicted a response of the electrochemical test cell 61 that varies as a function of the capacitance of the electrochemical test cell ($C_{CELL}$), resistance of the electrochemical test cell ($R_{CELL}$), and the strip resistance ($R_{STRIP}$) shown here in FIG. 8A. As can be seen in FIG. 8A, when the strip resistor is assumed to be about zero ohm, the predicted or referential capacitive response of the electrochemical test cell 61 (denoted by line 700) is generally linear (approximately 435 nanoFarad) over a range of the test cell resistance from about 120 kilo-ohms to about 20 kilo-ohms at which point the predicted or referential capacitive response increases almost exponentially to approximately 450 nanoFarads. When the strip resistance is assumed to be about 50 ohms, the predicted or referential capacitive response 702 of the electrochemical test cell 61 is generally linear over the resistance of the electrochemical test cell 61 from about 120 kilo-ohms to about 20 kilo-ohms at which point the predicted or referential capacitive response increases non-linearly but not to the extent of the capacitive response 700 with about zero strip resistance. When the strip resistance is assumed to be about 100 ohms, the predicted or referential capacitive response 704 of the electrochemical test cell 61 is generally linear over the resistance of the test cell 61 from about 120 kilo-ohms to about 20 kilo-ohms at which point the predicted or referential capacitive response decreases somewhat non-linearly. When the strip resistance is assumed to be about 100 ohms, the predicted or referential capacitive response 704 of the test cell 61 is generally linear over the resistance of the test cell 61 from about 120 kilo-ohms to about 20 kilo-ohms at which point the predicted or referential capacitive response decreases exponentially. In all cases of $R_{STRIP}$ values, the capacitance of the cell converges toward a generally common value when $R_{CELL}$ is about 100 kilo-Ohms and generally diverges depending on the $R_{STRIP}$ values from about 20 kilo-Ohms to about zero Ohm.

On the other hand, the actual capacitive and resistive responses in FIG. 8B from representative test strips of FIG. 3A are quite different from the referential capacitive/resistive responses of FIG. 8A. In particular, the capacitive responses do not converge toward a common capacitive value at the higher value of $R_{CELL}$. Yet the capacitive responses of the actual strip exhibited, at the low end of the resistance of $R_{CELL}$, a contrary behavior to the referential or predicted model of FIG. 8A by converging toward a generally common value of about 590 nanoFarad at the Rcell of about zero Ohms in FIG. 8B.

This anomaly in the behavior of $C_{CELL}$ at different values of $R_{CELL}$ was further investigated. A closer look at how the alternating signal was sampled showed what applicant believes is the reason for such anomaly. Specifically, the referential model utilizes a pure sine wave whereas the actual wave 900 is generated piecewise with 64 distinct current samples per wave, which is shown here in FIG. 9A. Because the wave 900 of FIG. 9A includes steps rather than a smooth line, this is believed to produce a different response of the measurement circuit that turns out to be highly dependent on $R_{STRIP}$.

Figure 9A:
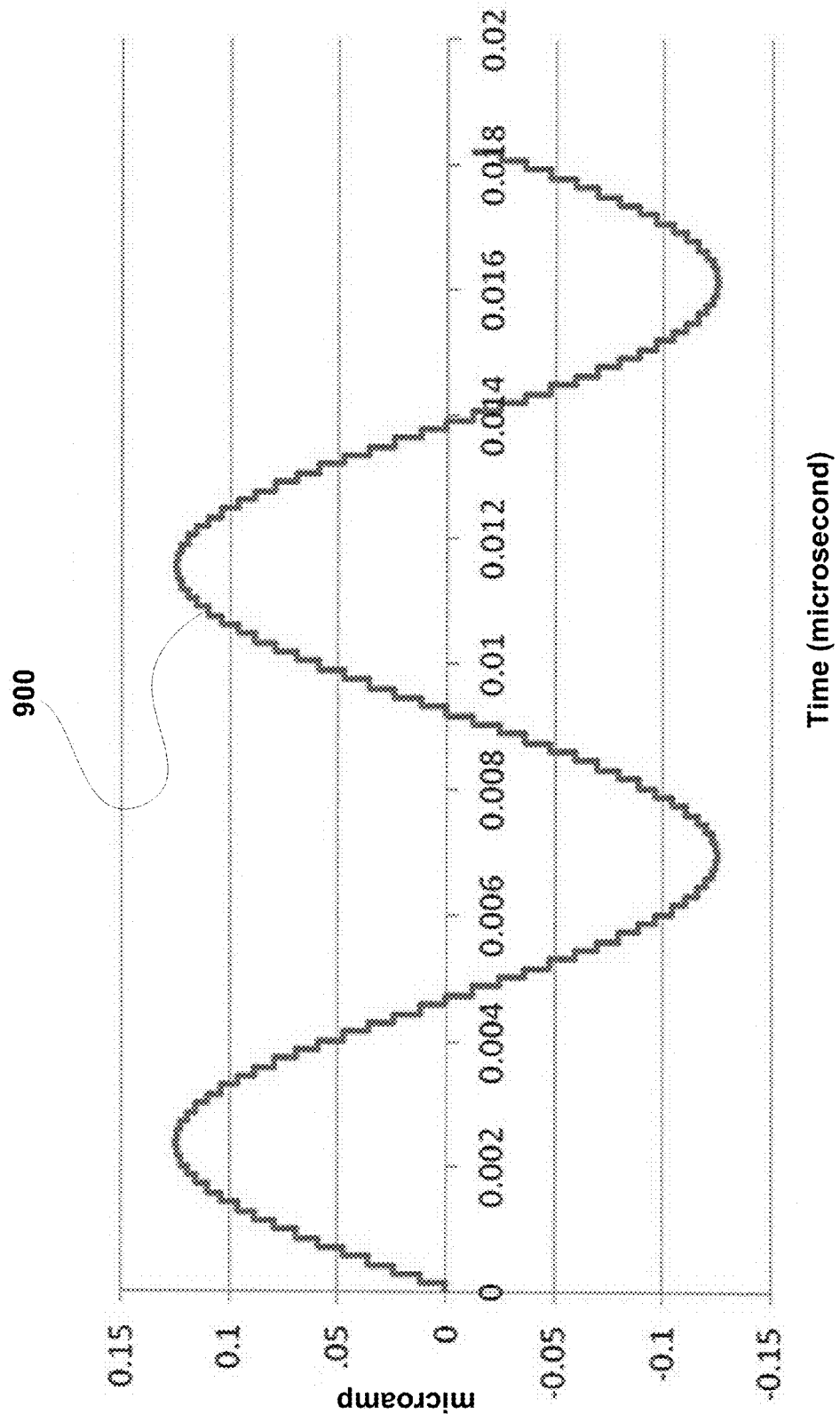
FIG. 9A illustrates an output osciallating signal as sampled by the system showing that the signal is generated by 64 distinct current samples giving the output signal a piecewise or stepwise signal.
Figure 9B:
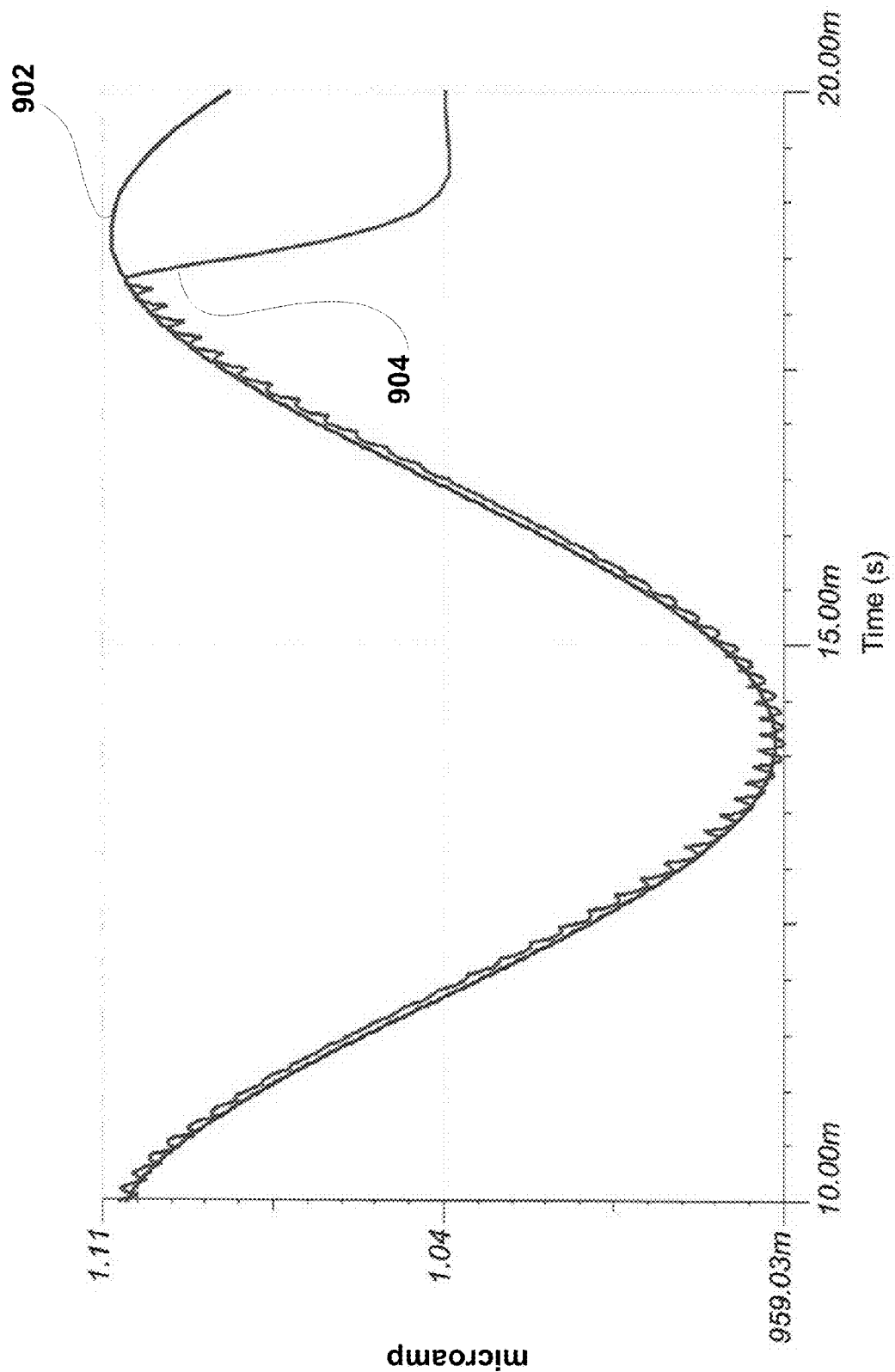
FIG. 9B shows an overlay of an actual sampled oscillating signal 904 as compared to a referential oscillating output signal 902 where the sampled signal is from a strip with high strip resistance.

Taking $R_{STRIP}$ to be about 200 Ohms, it can be seen in FIG. 9B that a theoretical output given excitation via a pure sine wave is a smooth continuous line 902 whereas the stepped saw-tooth line 904 is the output using a stepped wave signal, such as for example, the piecewise signal 900 in FIG. 9A. It can be seen that depending on the timing of when the piecewise response 904 is measured or sampled, the amplitude and phase measurements can change somewhat. It is believed that the driver to this anomaly between FIG. 8A and FIG. 8B is capacitance sensitivity to strip resistance $R_{STRIP}$ due to amplitude measurement inaccuracies. In this example with $R_{STRIP}$ being 200 Ohm, the phase difference can be seen to be somewhat insignificant to have a serious effect on measurements.

Figure 9C:
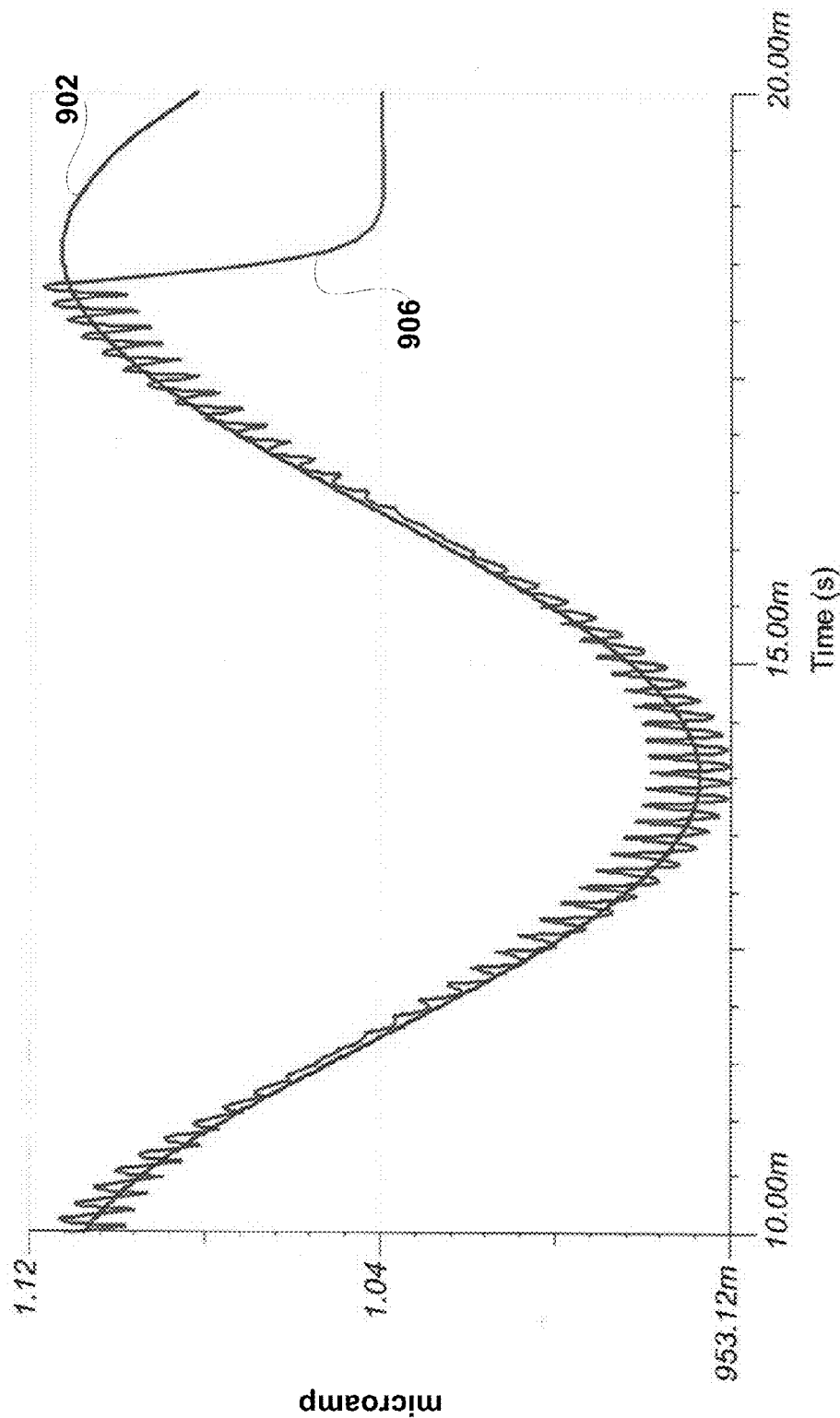
FIG. 9C shows an overlay of an actual sampled oscillating signal 906 as compared to the referential output signal 902 where the sampled signal 906 is from a strip with lower strip resistance as compared to strip resistance of FIG. 9B.

However, when $R_{STRIP}$ is set to about zero Ohm, the phase difference can be significant. As seen with respect to FIG. 9C, the piecewise like response 906 (which appears to have an inverted wave rectification) can, depending on where the response 906 is sampled can give a difference in output of up to about 20%. This difference is believed to be substantial in causing larger capacitance measurement errors. Applicant notes that when the resistance of the cell, $R_{CELL}$, is reduced, the amplitude of the disturbances due to the piecewise wave 900 also reduces, which is believed to be why the capacitance measurements tend to converge to a single capacitive value when $R_{CELL}$ is about 5 kilo-Ohm.

To compensate for this effect, it is believed that the piecewise output signal should be sampled at the right time after a step change of the piecewise wave 906. As shown in FIG. 9D, the piecewise wave 906 tends to lag or lead a pure wave 902 during a change in direction of the wave 906 as compared to a pure wave 902. Taking an enlarged portion of FIG. 9D, shown here in FIG. 9E, it can be seen that there is a time differential $\Delta t$ between a peak 908 of the piecewise wave 906 and where the piecewise wave 906 crosses over the pure wave 902 at cross-over point 910.

Figure 9F:
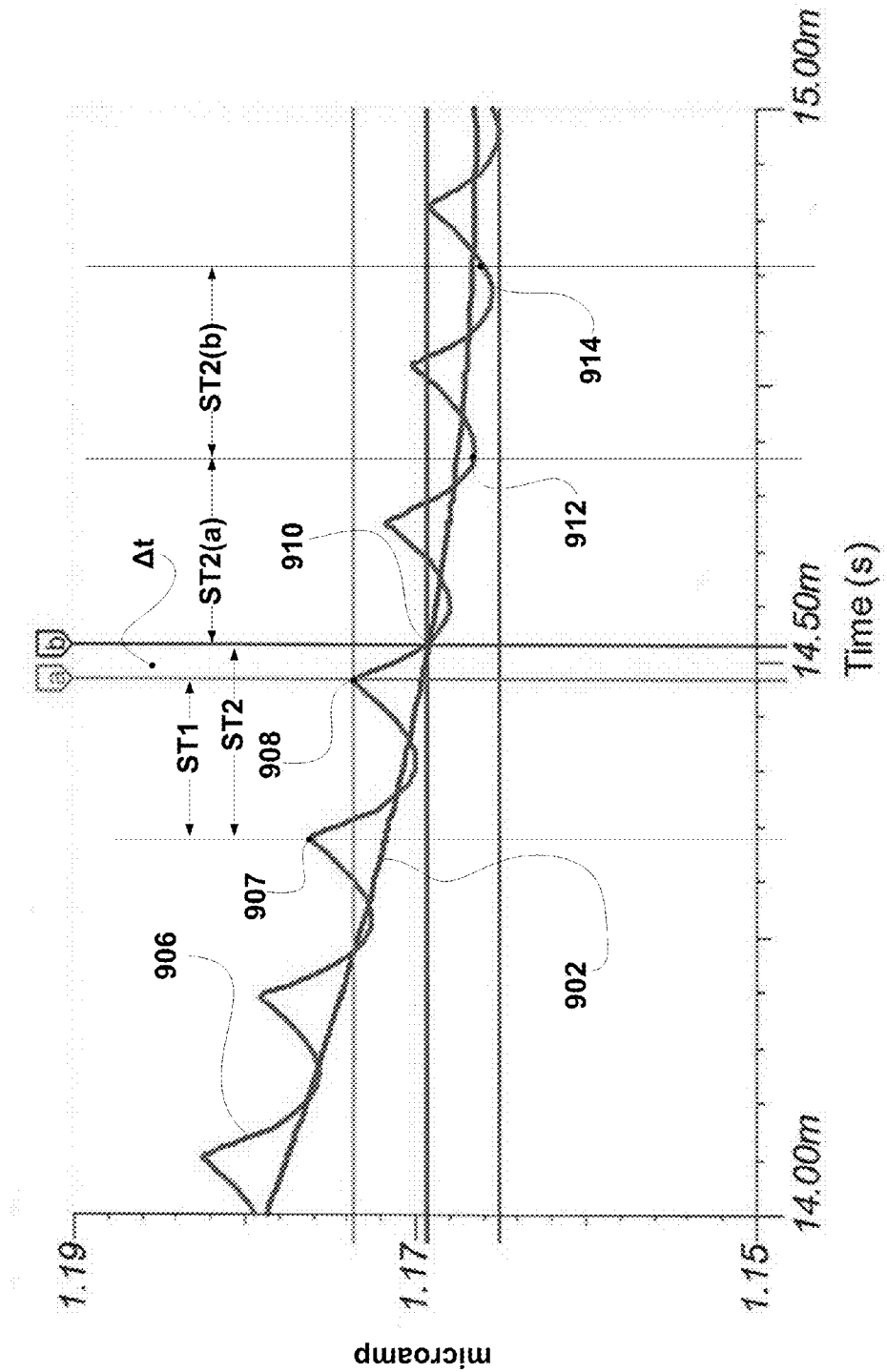
FIG. 9F illustrates graphically how the a first sampling time interval is modified by a time offset to provide for a second sampling-time interval which allows for more accurate capacitance measurements.

From this discovery of the source of the anomaly, applicant proceeded to carry out experiments to measure this time differential $\Delta t$ using a range of values for $C_{CELL}$, $R_{STRIP}$ and $R_{CELL}$ with reference to FIG. 9F and Table 1. In FIG. 9F, the reference "a" indicates the peak 908 at which the piecewise changes step and reference "b" indicates the desired sampling point where the output of the gain amp stage 314 matches the theoretical wave. The measurements were made at a plurality of points in both the positive and negative phases of the sine wave. The overall results are shown in Table 1, which gives a good idea of the boundary conditions for variations in the strip and meter system.

From Table 1, an average value can be calculated from the various boundary conditions to give a preferable sampling timing for a representative system. Applicant believes that the offset timing should be about 20% of the duration of a step change from peak-to-peak of the wave 906. For this particular example, with the driving frequency of about 109 Hz and 64 samples per cycle of the wave, 20% of a duration of a step change of 143 microseconds is about 28 microseconds. It is noted, however, other values from 5% to 40% (or about 17 microseconds to about 38 microseconds) will also work, depending on the driving frequency, sampling rate, duration of a step change, and the meter and strip system in use.

TABLE 1

| $C_{cell}$ (nF) | $R_{strip}$ (Ohm) | $R_{cell}$ (Ohm) | $\Delta t$ (microsecs.) | $\Delta t$ (microsecs.) |
|---|---|---|---|---|
| 400 | 100 | 100K | 26.06 | 21.17 |
| 700 | 100 | 100K | 26.06 | 17.92 |
| 400 | 200 | 100K | 26.06 | 19.54 |
| 700 | 200 | 100K | 27.69 | 19.54 |
| 400 | 100 | 5K | 32.51 | 28.95 |
| 700 | 100 | 5K | 37.86 | 26.73 |
| 400 | 200 | 5K | 42.32 | 31.18 |
| 700 | 200 | 5K | 27.73 | 33.41 |

Based on the above, applicant has discovered a method of determining capacitance of a biosensor chamber where the biosensor may have two electrodes disposed in the chamber and coupled to a microcontroller. After initiating an electrochemical reaction of a sample upon deposition of the sample in the biosensor chamber, the method includes applying an oscillating signal of a predetermined frequency to the chamber; ascertaining a first sampling-time interval for measurement of an output signal based on a predetermined sampling rate per cycle of the output signal at the predetermined frequency; sampling the output signal from the chamber at a second sampling-time interval different than the first sampling-time interval such that a magnitude of each sampled output signal is measured at each succession of the second sampling-time interval instead of at the first time interval; determining a phase angle between an output signal and the oscillating input signal from the chamber based on the sampled output signal of the sampling step; and calculating a capacitance of the chamber from the phase angle.

In the applying step, the oscillating signal may be an alternating current ("AC") signal or a multi-directional signal and the predetermined frequency may be about 109 Hertz. In the ascertaining step, a first sampling-time interval is obtained based on the predetermined frequency and a number of sample measurements taken for each cycle of the signal. As an example, in FIG. 6A, the predetermined frequency of the input signal is about 109 cycles per second, which means that one cycle of the output signal takes about 0.009 second. If the desired sampling rate is N, for example, 64 samples per second, then each sample (e.g., S1, S2, S3 . . . Sn) is taken by dividing the time taken by one wave (0.009 seconds) over N (or 64) samples resulting in a sampling time of about 143 microseconds. In other words, the magnitude of the output response 602 is sampled every 143 microseconds and the measurement stored. In the sampling step, the magnitude of the output signal is measured at a second sampling time interval different from the first sampling-time interval in order to ensure that the magnitude of the sampled output response does not deviate from a theoretical continuous output signal (e.g., pure sine wave output). The second sampling time interval can be a predetermined time offset from the first time interval or a percentage of the first sampling-time interval. The percentage can be from about 5% to about 30%. Alternatively, a time duration from peak-to-peak of the piecewise output signal (e.g., 906 in FIG. 9E) can be used to set the first sampling-time interval ST1. For example, as shown in FIG. 9E, a time duration from peak 908 and peak 912 can be used to set the first sampling-time duration ST1 or an average of the peak-to-peak duration of all the peaks in one wave of the signal 906 can be used to set the first sampling-time duration. The second sampling time interval ST2 can be a percentage increase (or decrease depending the direction of the wave) of the first sampling-time interval ST1. In one embodiment, the percentage can be any value from about 5% to about 30% and preferably about 20%. Once the second sampling time interval is determined, the magnitude of the output signal 906 (FIG. 9F) is measured at each succession of the second sampling time interval ST2 with two succeeding time intervals ST2 shown here in FIG. 9F as ST2(a) and ST2(b) where the magnitude of the output signal is sampled at 910, 912, 914 and so on. From the sampled magnitudes of the output signal, the phase angle difference between the input and output signal is determined and the capacitance can be measured as described earlier. Thus, applicant's use of the offset timing allow for the sampling interval to smooth out the differences in the magnitudes of the sampled output signal, which coincidentally, allow the modified sampling-time interval to coincide as close to what a continuous (non-piecewise) output signal would be for more accurate measurement purposes.

Applicant believes that one useful technique to test the usefulness of a capacitance measurement of physiological fluid is to do such measurements with interfering substances in the sample. Interferants are materials or substances that are not considered to be part of the physiological fluid but yet may interfere with the ability of biosensors to accurately measure the constituents of physiological fluid. One interferant that has been known to affect capacitance measurement is gentisic acid. That is, as increasing quantity of gentisic acid is added to the same batch of physiological fluid (in this case, blood), the measured capacitance changes substantially.

Although the exemplary embodiments, methods, and system have been described in relation to a blood glucose strip, the principles described herein are also applicable to any analyte measurement strips that utilize a physiological fluid on a reagent disposed between at least two electrodes.

As noted earlier, the microcontroller can be programmed to generally carry out the steps of various processes described herein. The microcontroller can be part of a particular device, such as, for example, a glucose meter, an insulin pen, an insulin pump, a server, a mobile phone, personal computer, or mobile hand held device. Furthermore, the various methods described herein can be used to generate software codes using off-the-shelf software development tools such as, for example, C or variants of C such as, for example, C+, C++, or C-Sharp. The methods, however, may be transformed into other software languages depending on the requirements and the availability of new software languages for coding the methods. Additionally, the various methods described, once transformed into suitable software codes, may be embodied in any computer-readable storage medium that, when executed by a suitable microcontroller or computer, are operable to carry out the steps described in these methods along with any other necessary steps.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining capacitance of a biosensor chamber having two electrodes disposed in the chamber and coupled to a microcontroller, the method comprising:
  initiating an electrochemical reaction of a sample upon deposition of the sample in the biosensor chamber;
  applying an oscillating signal of a predetermined frequency to the chamber;
  ascertaining a first sampling-time interval for measurement of an output signal based on a predetermined sampling rate per cycle of the output signal at the predetermined frequency;
  sampling the output signal from the chamber at a second sampling-time interval different than the first sampling-time interval such that a magnitude of each sampled output signal is measured at each succession of the second sampling-time interval instead of at the first time interval;

determining a phase angle between an output signal and the oscillating input signal from the chamber based on the sampled output signal of the sampling step; and calculating a capacitance of the chamber from the phase angle.

2. The method of claim 1, in which the second sampling-time interval is based on a predetermined offset time with respect to the first sampling-time interval.

3. The method of claim 2, in which the first sampling-time interval comprises a duration between each step change in magnitude of the output signal.

4. The method of claim 2, in which the offset time comprises a percentage of the first sampling-time interval.

5. The method of claim 4, in which the percentage comprises a range from about 5% to about 30% of the first sampling-time interval.

6. The method of claim 5, in which the calculating comprises determining a difference in the angle between the oscillating input current and the output current as the phase angle.

7. The method of claim 1, in which the ascertaining comprises:
determining a duration for one wave of the signal at the predetermined frequency;
dividing the duration over a number of measurement samples for each wave to obtain a time duration; and
setting the first sampling-time interval as being generally equal to the time duration.

8. The method of claim 1, in which the ascertaining comprises:
evaluating the output signal to determine a time duration between each step change of the output signal; and
setting the first sampling-time interval as being generally equal to the time duration.

9. The method of one of claim 7 or claim 8, in which the offset time comprises a percentage of the first sampling-time interval.

10. The method of claim 9, in which the percentage comprises a range from about 5% to about 30% of the first sampling-time interval.

11. The method of claim 1, in which the calculating comprises calculating capacitance with a phase angle compensation to account for phase shift in a circuit used to sample the output signal.

12. The method of one of claim 1 or claim 11, in which the calculating comprises calculating capacitance with an equation of the form:

$$C \approx |i_T \sin(\Phi + \Phi_{COMP})|/2\pi f V$$

where:
C≈capacitance;
$i_T$≈total current;
Φ≈phase angle between total current and resistor current;
$\Phi_{COMP}$≈phase angle compensation;
f≈frequency; and
V≈voltage.

13. The method of claim 12, in which the phase angle compensation comprises any value from about 3 degrees to about 20 degrees.

14. The method of claim 13, in which the phase angle compensation comprises about 11 degrees.

15. The method of claim 12, in which the calculating comprises:
sampling a plurality of current outputs from the chamber over one cycle of the frequency;
obtaining a mean of sampled current output;
subtracting the mean from each sampled current of the plurality of current outputs; and
extracting root-mean-squared value of all negative values from the subtracting to provide for the total current output.

16. The method of claim 15, in which the calculating comprises:
determining from the sampling, at least one cross-over point of the current from negative to positive values; and
interpolating proximate the at least one cross-over point of the current to determine a first angle at which the current changes from positive to negative or negative to positive.

17. The method of claim 16, in which the interpolating the at least one cross-over point of the current comprises:
interpolating another cross-over point from the sampling to determine another angle at which the current changes from positive to negative or negative to positive; and
subtracting from the another angle approximately 180 degrees to provide for a second angle.

18. The method of claim 17, in which the subtracting further comprises calculating an average of the first and second angles.

19. An analyte measurement system comprising:
An analyte test strip including:
a substrate having a reagent disposed thereon;
at least two electrodes proximate the reagent a in test chamber of the test strip;
an analyte meter including:
a strip port connector disposed to connect to the two electrodes;
a power supply; and
a microcontroller electrically coupled to the strip port connector and the power supply, the microcontroller being programmed to:
(a) initiate an electrochemical reaction in the biosensor chamber; apply an oscillating voltage of a predetermined frequency to the chamber;
(b) ascertain a first sampling-time interval for measurement of an output signal based on a predetermined sampling rate per cycle of the output signal at the predetermined frequency;
(c) sample the output signal from the chamber at a second sampling-time interval different than the first sampling-time interval such that a magnitude of each sampled output signal is measured at each succession of the second sampling-time interval instead of at the first time interval;
(d) determine a phase angle between a current output and the oscillating voltage from the chamber based on the sampled output signal; and
(e) calculate a capacitance of the chamber based on the determined phase angle.

20. The system of claim 19, in which the second sampling-time interval is based on a predetermined offset time with respect to the first sampling-time interval.

21. The system of claim 20, in which the first sampling-time interval comprises a duration between each step change in magnitude of the output signal.

22. The system of one of claim 20 or claim 21, in which the offset time comprises a percentage of the first sampling-time interval.

23. The system of claim 22, in which the percentage comprises a range from about 5% to about 30% of the first sampling-time interval.

* * * * *